United States Patent [19]

Nogusa et al.

[11] Patent Number: 5,688,931
[45] Date of Patent: Nov. 18, 1997

[54] POLYSACCHARIDE DERIVATIVES AND DRUG CARRIERS

[75] Inventors: Hideo Nogusa; Hiroshi Hamana; Toshiro Yano; Masahiro Kajiki; Keiji Yamamoto, all of Chiba-ken; Satoshi Okuno, Saitama-ken; Shuichi Sugawara, Chiba-ken; Nobukazu Kashima, Chiba-ken; Kazuhiro Inoue, Chiba-ken, all of Japan

[73] Assignee: Drug Delivery System Institute, Ltd., Tokyo-to, Japan

[21] Appl. No.: 325,296

[22] PCT Filed: Feb. 28, 1994

[86] PCT No.: PCT/JP94/00322

§ 371 Date: Dec. 28, 1994

§ 102(e) Date: Dec. 28, 1994

[87] PCT Pub. No.: WO94/19376

PCT Pub. Date: Sep. 1, 1994

[30] Foreign Application Priority Data

Feb. 26, 1993 [JP] Japan .................... 5-038635

[51] Int. Cl.$^6$ .................. C08B 37/02; C08B 37/08; C07H 13/02; C07K 5/00
[52] U.S. Cl. .................. 536/20; 536/21; 536/112; 536/115; 536/119; 536/123.1; 536/123.12; 530/300; 530/322
[58] Field of Search .................. 530/322, 300; 536/20, 21, 119, 123.1, 123.12, 112

[56] References Cited

U.S. PATENT DOCUMENTS 5,463,022 10/1995 Inoue et al. .................. 536/20

FOREIGN PATENT DOCUMENTS

| 397307 | 11/1990 | European Pat. Off. |
| 0506976 | 10/1992 | European Pat. Off. |
| 0526649 | 2/1993 | European Pat. Off. |

OTHER PUBLICATIONS

Tokura et al., "Carboxymethyl-Chitin as a Drug Carrier of Substained Release", Carbohydrate Polymers 13 (1990), 273–281.

Carbohydrate Rearch, vol. 245, issued 1993, Dean et al, "Synthesis of Multivalent β–Lactosyl Clusters as Potential Tumor Metastasis Inhibitors", pp. 175–192.

Primary Examiner—John Kight
Assistant Examiner—Everett White
Attorney, Agent, or Firm—Wenderoth, Lind & Ponack

[57] ABSTRACT

A novel polysaccharide derivative, a drug carrier comprising a novel polysaccharide derivative, and a drug complex are disclosed. The polysaccharide derivative according to the present invention comprises a polysaccharide having a carboxyl group in which a peptide chain is introduced at a part or all of the carboxyl groups of the polysaccharide. The peptide chain comprises 1–8 amino acids which may be the same or different. A part or all of the amino groups in the peptide chain which are not involved in the linkages with the carboxyl groups of the polysaccharide or the carboxyl groups in the peptide chain may form an acid amide linkage or an ester linkage with a carboxyl group, an amino group or a hydroxyl group of a third compound such as drugs. The polysaccharide derivative has a property of accumulating in a high amount at a tumor, and thus can deliver efficiently a drug which has a side-effect or a limited sustainment of the drug efficacy to the tumor.

16 Claims, 11 Drawing Sheets

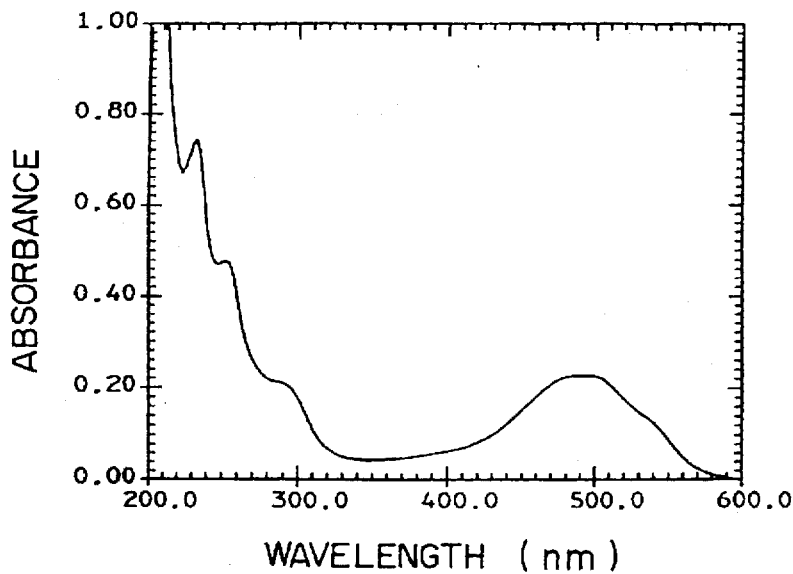
F I G. 15
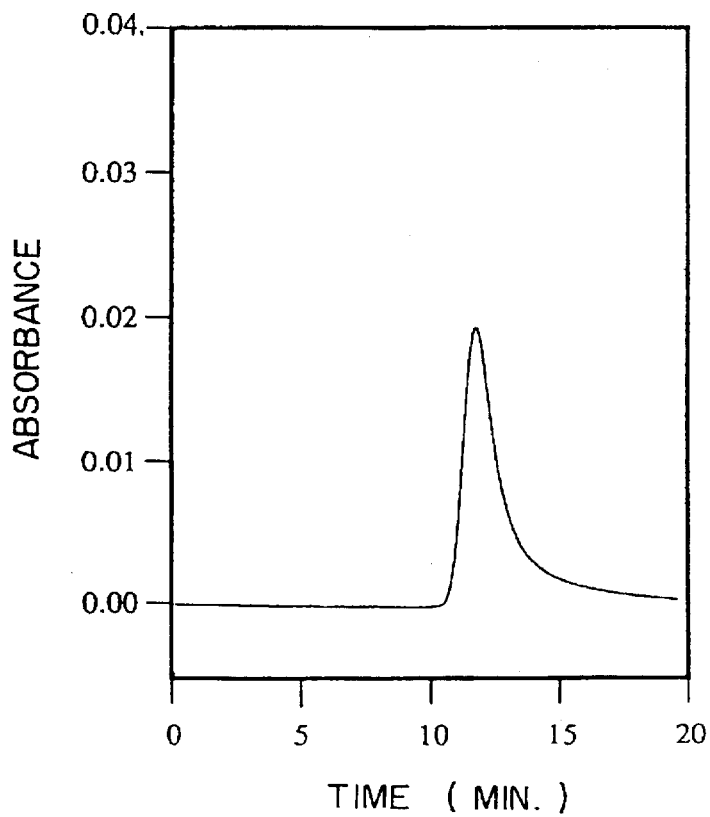
F I G. 16

5,688,931

POLYSACCHARIDE DERIVATIVES AND DRUG CARRIERS

BACKGROUND OF THE INVENTION

1. Field of the Invention

The present invention relates to a drug carrier comprising a novel polysaccharide and a drug complex. More particularly, the present invention relates to a drug carrier comprising a polysaccharide combined with a peptide, and a drug complex comprising the drug carrier and a drug introduced into the drug carrier.

2. Related Art

An attempt to use a water-soluble polymer as a carrier for a drug has hitherto been made especially in the field of a pharmaceutical preparation, and many related techniques for this purpose have been proposed in the art. In many of these proposals, use is made of cellulose derivatives such as carboxymethyl cellulose, hydroxypropyl cellulose and hydroxypropyl methylcellulose, and the dispersion and sustained release of the drug are intended by virtue of physical and chemical properties of these substances per se. While in these attempts the drug is mixed homogeneously with the cellulose derivatives as a carrier, the drug is not chemically bonded to the carrier.

In the so-called "drug delivery technique" wherein a drug is delivered by a necessary amount at a desired time to a target organ, when a water-soluble polymer is utilized as a carrier for a drug, the drug and the carrier should be chemically bonded to each other rather than being combined by mere mixing. There have been reported such attempts for polysaccharides in the following references 1), 2) and 3). Reference 1) discloses the technique to bond a carboxylated dextran with mitomycin C. Reference 2) discloses the technique to bond mannan with mitomycin C. Moreover, reference 3) discloses the technique to bond mannan with bleomycin.

1) Hitoshi Sezaki, Yakugaku Zasshi, 109, 611–621 (1989),
2) Proceeding of the 49th Japanese Cancer Association (1990) p. 425, No. 2155,
3) Proceeding of the 49th Japanese Cancer Association (1990) p. 425, No. 2154.

It is, however, the present situation that the drug delivery technique by means of chemical bond between a drug and a carrier has not sufficiently been developed for use yet.

SUMMARY OF THE INVENTION

The present inventors have examined the possibility for use of polysaccharides as a drug carrier. As a result, it has been found that a polysaccharide derivative in which a peptide chain is introduced into a polysaccharide exhibits an excellent property as a drug carrier.

Therefore, an object of the present invention is to provide a novel drug carrier on which a drug is conjugated through chemical bond and which is capable of drug delivery, and a drug complex of the drug carrier and a drug.

Thus, the present invention provides a polysaccharide derivative comprising a polysaccharide having a carboxyl group into which a peptide chain is introduced at a part or all of the carboxyl groups of the polysaccharide, the peptide chain comprising 1–8 amino acids where the amino acids may be the same or different, wherein a part or all of the amino groups in the peptide chain which are not involved in the linkage with the carboxyl groups of the polysaccharide or a part or all of the carboxyl groups in the peptide chain may form an acid amide linkage or an ester linkage with a carboxyl group, an amino group or a hydroxyl group of a third compound having the carboxyl group, the amino group or the hydroxyl group, and a salt thereof.

The polysaccharide derivative according to the present invention has a property of highly accumulating at a tumor. Therefore, the compound can efficiently deliver to a tumor a drug having a side effect or limited sustainment of its efficacy against tumor.

In addition, the polysaccharide derivative according to the present invention has a property of gradually distributing a drug in a body, so that the drug concentration can be highly retained in blood for a long period.

Accordingly, the present invention provides a drug carrier and a drug complex comprising the polysaccharide derivative.

In the present invention, the term "polysaccharide containing a carboxyl group" means, a polysaccharide which naturally contains a carboxyl group in its structure such as hyaluronic acid, pectic acid, alginic acid, chondroitin or heparin. In addition, the term also means a polysaccharide naturally containing no carboxyl groups such as pullulan, dextran, mannan, chitin, inulin, levan, xylan, arabin, mannoglucan or chitosan, in which the hydrogen atoms in a part or all of the hydroxyl groups are substituted by a carboxy $C_{1-4}$ alkyl group or in which at a part or all of the hydroxyl groups a polybasic acid is introduced through an ester linkage.

The term "polysaccharide derivative" herein means both a drug carrier and a drug complex in which the carrier is bonded with a drug. Furthermore, the term "acid amide linkage" herein means a urethane linkage and a urea linkage inclusive.

BRIEF DESCRIPTION OF THE DRAWINGS

FIG. 15 illustrates an ultraviolet-visible absorption spectrum of sodium N-acetyl-de-N-sulfated heparin-3'-N-(Gly-Gly-Phe-Gly)-DXR (50) obtained in Example 19 (concentration: 257 µg/ml, solvent: water);

FIG. 16 illustrates an elution pattern by gel filtration of sodium N-acetyl-de-N-sulfated heparin-3'-N-(Gly-Gly-Phe-Gly)-DXR (50) obtained in Example 19 (detected by visible absorption at 478 nm);

DETAILED DESCRIPTION OF THE INVENTION

Polysaccharide Derivatives

Figure 1:
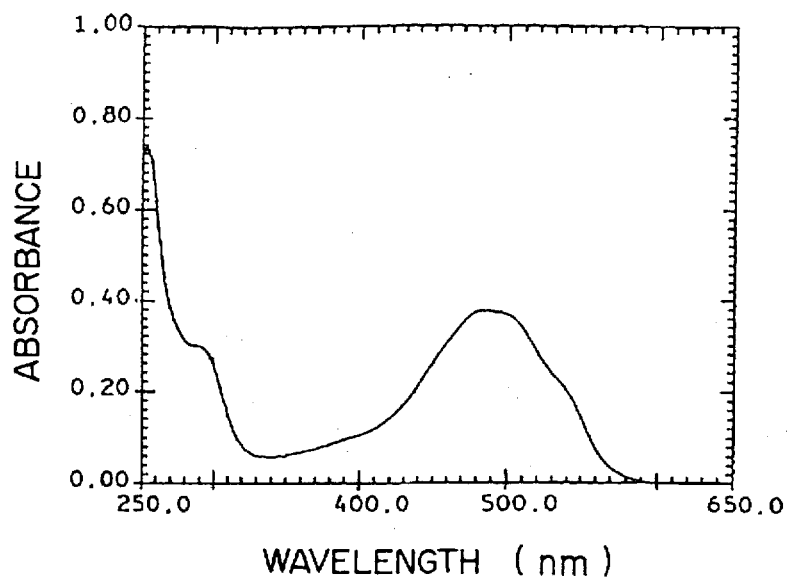
FIG. 1 illustrates an ultraviolet-visible absorption spectrum of sodium carboxymethylpullulan-3'-N-(Gly-Gly-Phe-Gly)-DXR (23) obtained in Example 1 (concentration: 300 µg/ml, solvent: water)

The polysaccharide derivative according to the present invention includes first a polysaccharide as a basic skeleton which naturally contains a carboxyl group.

The polysaccharide derivative according to the present invention also includes a polysaccharide as a basic skeleton which naturally contains no carboxyl group. The polysaccharide derivatives comprising as basic skeleton the polysaccharide containing no carboxyl group should have a structure in which the hydrogen atoms in a part or all of the hydroxyl groups are substituted by a carboxy $C_{1-4}$ alkyl group or in which at a part or all of the hydroxyl groups a polybasic acid is introduced through an ester linkage.

The polysaccharide derivative according to the present invention comprises a structure in which a peptide chain is introduced into the carboxyl group in the above polysaccharide.

The alkyl part of the carboxy $C_{1-4}$ alkyl group with which the hydrogen atom of the hydroxyl groups in the polysaccharide is substituted may be a linear or branched chain. The carboxy $C_{1-4}$ alkyl group preferably includes, for example, carboxymethyl, carboxyethyl, carboxypropyl, carboxyisopropyl and carboxybutyl.

The "polybasic acid" which is introduced into the hydroxyl group of the polysaccharide through an ester linkage means an acid having at least two protons which can be donated in a molecule, i.e., an acid having a basicity of two or more. The polybasic acid preferably includes, for example, malonic acid, succinic acid, glutaric acid, adipic acid, maleic acid, fumaric acid, citraconic acid, cis-aconitic acid, L-aspartic acid, L-glutamic acid and diglycolic acid.

In this connection, the introduction degree of the carboxyalkyl group or the polybasic acid can be represented by the "substitution degree" which is defined as a number of the carboxyalkyl group or the polybasic acid per sugar residue. The number includes the groups that the peptide chain is further introduced into the carboxyalkyl group or the polybasic acid. Thus, the "degree of substitution" can be represented as follows:

$$\text{Degree of substitution} = \frac{\text{Total number of the carboxyalkyl groups or the polybasic acids in molecule}}{\text{Total number of the sugar residue in molecule}}$$

In this context, when the carboxyalkyl group is a carboxymethyl group, the substitution degree may be expressed as "the degree of carboxymethylation", and when the polybasic acid is succinic acid, it may be expressed as "the degree of succinylation".

When the polysaccharide is pullulan, of which the hydroxyl groups are all substituted, the degree of substitution is 3. The degree is preferably 0.1 or more.

When the polysaccharide is chitin, of which the hydroxyl groups are all substituted, the degree of substitution is 2. The degree is preferably 0.1 or more.

When the polysaccharide is dextran, of which the hydroxyl groups are all substituted, the degree of substitution is 3. The degree is preferably 0.1 or more.

When the polysaccharide is mannoglucan, of which the hydroxyl groups are all substituted, the degree of substitution is 3. The degree is preferably 0.1 or more.

It is necessary that the molecule of the polysaccharide derivative has at least one carboxyalkyl group or a polybasic acid except that the polysaccharide naturally has a carboxyl group. Therefore, compounds having a substitution degree of 0 are excluded from the polysaccharide derivative of the present invention.

According to the present invention, the peptide chain introduced into the polysaccharide comprises 1 to 8 amino acids which may be the same or different. The number of the amino acids is preferably two or more in consideration of the drug releasing property of the polysaccharide derivative. Moreover, the number is also preferably six or less in consideration of the complicated synthetic process of the peptide chain. The number is more preferably four or less.

The amino acids are not specifically limited, but are preferably a combination of two or more of the neutral amino acids which are different from each other according to the preferred embodiment of the present invention. Such peptide chains include, for example, an amino acid sequence -Phe-Gly- and a peptide chain containing this sequence of which the N-terminal side is linked to the carboxyl group of the polysaccharide.

Furthermore, the term "the peptide chain comprising amino acids" herein means not only a peptide chain comprising amino acids alone but also a peptide chain including a compound other than amino acids in the chain. For instance, a dibasic carboxylic acid such as succinic acid may be present within or in the terminal of the peptide chain. The amino acid in the peptide chain may also be α-amino acids as well as amino acid analogous compounds such as ε-aminocaproic acid or γ-aminobutyric acid. The peptide chain is generally bonded to the carboxyl group of the polysaccharide in the direction from the N-terminal. Alternatively, the linkage direction of the peptide chain may be reversed by attaching the amino acid other than the α-amino acids (for example the ε-amino group of lysine, when the peptide chain contains lysine) to the carboxyl group of the polysaccharide.

While the peptide chain may be introduced to all of the carboxyl groups of the polysaccharide, the degree of the introduction is preferably determined depending on the physico-chemical and pharmacological properties of a drug introduced into the peptide chain.

The amino acid sequence of the peptide chain should be selected so that the drug or its active molecule rapidly or in cases gradually is released by enzymes such as protease or peptidase in organs. The amino acids may be either a neutral amino acid, a basic amino acid or an acidic amino acid.

The amino group or the carboxyl group of the peptide which is not involved in the linkage with the carboxyl group of the polysaccharide may form an acid amide linkage or an ester linkage with the carboxyl group, the amino group or the hydroxyl group of a third compound.

The third compound includes, for example, a compound which can form a bond with the amino group or the carboxyl group at the terminal of the peptide to protect the peptide. In this type compound, the portion for protecting functional groups, i.e. the protective group, may be a group that is generally used for the protection of amino acids. For example, the group may include protective groups of an amino group such as a tert-butoxycarbonyl group and a p-methoxybenzyloxycarbonyl group, and the protective groups of a carboxyl group such as a lower alkoxy group (e.g. a tert-butyoxy group), a lower alkylimino group (e.g. a methylimino group) and a benzyloxy group.

When the third compound is a drug having an amino group, a carboxyl group or a hydroxyl group that is introduced into the polysaccharide derivative through an acid amide linkage or an ester linkage to form a drug complex, the complex is included within the present invention.

The polysaccharide derivative according to the present invention can be present as a salt thereof, which is preferably a pharmaceutically acceptable salt in consideration of its uses. Such a salt includes alkali metal or alkaline earth metal salts such as a sodium salt, a potassium salt and a calcium salt and amino acid salts such as an arginine salt and a lysine salt.

The polysaccharide derivative according to the present invention can be used as a drug carrier on which a drug is supported for delivering it to, for example, tumor tissues. The polysaccharide derivative according to the present invention preferably releases the drug in a body and does not stay in the body for a long period.

Drugs such as an anti-tumor agent can be introduced into the peptide chain of the polysaccharide derivative of the present invention by use of the amino group or the carboxyl group of a terminal amino acid in the peptide chain.

For example, the drug having an amino group may form an acid amide linkage together With the carboxyl group of the terminal amino acid. The drug having an alcoholic hydroxyl group may form an ester linkage together with the carboxyl group of the terminal amino acid. The drug having a carboxyl group may form a linkage with an amino group of the terminal amino acid.

Specifically, these types of drugs include drugs having an amino group such as doxorubicin, daunorubicin, mitomycin C and bleomycin, and drugs having an alcoholic hydroxyl group such as cyclocytidine, vincristine, vinblastine and adrenaline. The drugs having a carboxyl group include methotrexate, bumetanide, furocemide and dinoprost.

It is also possible to use, in addition to these drugs, a drug converted into a derivative which can form together with a peptide chain an acid amide linkage or an ester linkage.

The degree of introducing the drug into the polysaccharide ("drug content") is appropriately determined depending on the drugs and the polysaccharides. The preferred ranges are as follows:

When the polysaccharide is pulullan, the drug content is preferably in the range from 0.1 to 30% by weight, particularly from 1 to 10% by weight.

When the polysaccharide is chitin, the drug content is preferably in the range from 0.1 to 30% by weight, particularly from 1 to 10% by weight.

When the polysaccharide is dextran, the drug content is preferably in the range from 0.1 to 30% by weight, particularly from 1 to 10% by weight.

When the polysaccharide is mannoglucan, the drug content is preferably in the range from 0.1 to 30% by weight, particularly from 1 to 10% by weight.

When the polysaccharide is N-acetyl-de-N-sulfated heparin, the drug content is preferably in the range from 0.1 to 30% by weight, particularly from 1 to 10% by weight.

When the polysaccharide is hyaluronic acid, the drug content is preferably in the range from 0.1 to 30% by weight, particularly from 1 to 10% by weight.

The complex, i.e., the polysaccharide derivative into which a drug has been introduced, can also be formed into its salt. Examples of the suitable salt include alkali metal or alkaline earth metal salts such as a sodium salt, a potassium salt and a calcium salt, and amino acid salts such as an arginine salt and a lysine salt.

The polysaccharide derivative in which the polysaccharide is pulullan, chitin, dextran, mannoglucan, N-acetyl-de-N-sulfated heparin or hyaluronic acid will now be explained below.

The polysaccharide derivative in which the polysaccharide is pulullan (referred to hereinafter as "the pulullan derivative") comprises the repeating unit represented by the formula (I):

$$\left[ \begin{array}{ccc} CH_2 & CH_2OR^4 & CH_2OR^7 \\ \diagup O & \diagup O & \diagup O \\ R^1O \diagdown OR^2 \diagdown_O \diagdown OR^5 \diagdown_O \diagdown OR^8 \diagdown_O \\ OR^3 & OR^6 & OR^9 \end{array} \right] \quad (I)$$

in which, $R^1$–$R^9$, which may be the same or different, respectively represent a hydrogen atom, a group —$(CH_2)_m$—CO—X, a group —CO—$(CH_2)_n$—CO—X, or a group —CO—A—CO—X, where —CO—A—CO— represents a polybasic acid moiety of a polybasic acid from which the hydroxyl groups of two carboxyl groups have been removed, X represents a hydrogen atom or a peptide chain comprising 1–8 amino acids which may be the same or different, a part or all of the amino groups in the peptide chain which are not involved in the linkages with the carboxyl groups of the polysaccharide or the carboxyl groups in the peptide chain may form an acid amide linkage or an ester linkage with a carboxyl group, an amino group or a hydroxyl group of a third compound having the carboxyl group, the amino group or the hydroxyl group, m represents an integer of 1–4, and n represents an integer of 1–4.

The pulullan derivative has preferably a molecular weight of the pulullan moiety in the range from $2\times10^3$ to $1\times10^6$, more preferably from $1\times10^4$ to $2\times10^5$.

In the pulullan derivative, the peptide chain is introduced preferably in a proportion from 0.01 to 3.0, more preferably from 0.01 to 0.1 per sugar residue.

The polysaccharide derivative in which the polysaccharide is chitin (referred to hereinafter as "the chitin derivative") comprises the repeating unit represented by the formula (II):

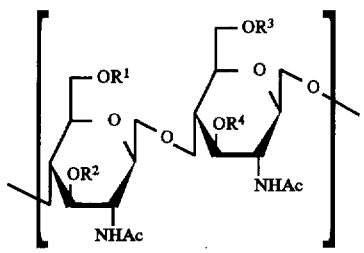

wherein $R^1$–$R^4$, which may be the same or different, respectively represent the groups as defined in the formula (I).

The chitin derivative has preferably a molecular weight of the chitin moiety in the range from $2\times10^3$ to $1\times10^6$, more preferably from $1\times10^4$ to $2\times10^5$.

In the chitin derivative, the peptide chain is introduced preferably in a proportion from 0.001 to 2.0, more preferably from 0.01 to 0.1 per sugar residue.

The polysaccharide derivative in which the polysaccharide is dextran (referred to as "the dextran derivative") comprises the repeating unit represented by the formula (III):

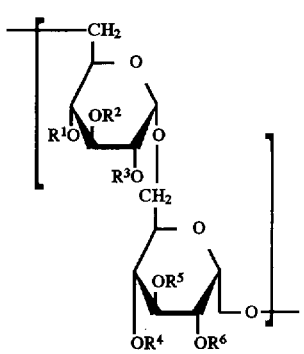

wherein $R^1$–$R^6$, which may be the same or different, respectively represent the groups as defined in the formula (I).

The dextran derivative has preferably a molecular weight of the dextran moiety in the range from $2\times10^3$ to $1\times10^6$, more preferably from $1\times10^4$ to $2\times10^5$.

In the dextran derivative, the peptide chain is introduced preferably in a proportion from 0.001 to 3.0, more preferably from 0.01 to 0.1 per sugar residue.

The polysaccharide derivative in which the polysaccharide is mannoglucan (referred to hereinafter as "the mannoglucan derivative") comprises the repeating unit represented by the formula (IV):

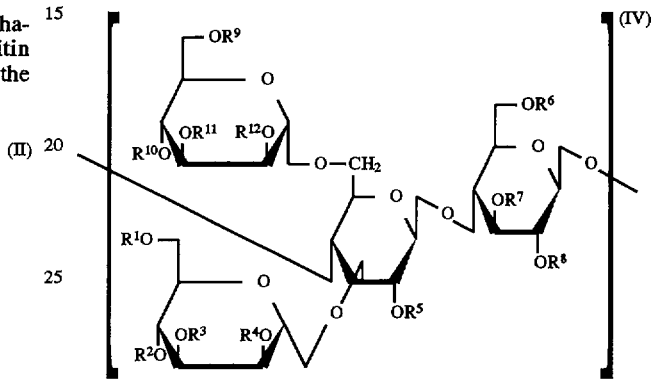

wherein $R^1$–$R^9$, which may be the same or different, respectively represent the groups as defined in the formula (I), and $R^{10}$–$R^{12}$, which may be the same or different, respectively represent the groups as defined in the groups $R^1$–$R^9$.

The aforementioned mannoglucan derivative has preferably a molecular weight of the mannoglucan moiety in the range from $2\times10^3$ to $1\times10^6$, more preferably from $1\times10^4$ to $2\times10^5$.

In the mannoglucan derivative, the peptide chain is introduced preferably in a proportion from 0.004 to 12.0, more preferably from 0.04 to 0.4 per repeating unit.

In the polysaccharide derivative according to the present invention, a position at which the carboxy alkyl group or the polybasic acid is introduced into may be the same as or different from positions of that in the adjacent saccharide units, provided that each of the saccharide units has a structure defined by any one of the formulae (I)–(IV).

The polysaccharide derivative in which the polysaccharide is N-acetyl-de-N-sulfated heparin (referred to hereinafter as "the heparin derivative") comprises the repeating unit represented by the formula (V):

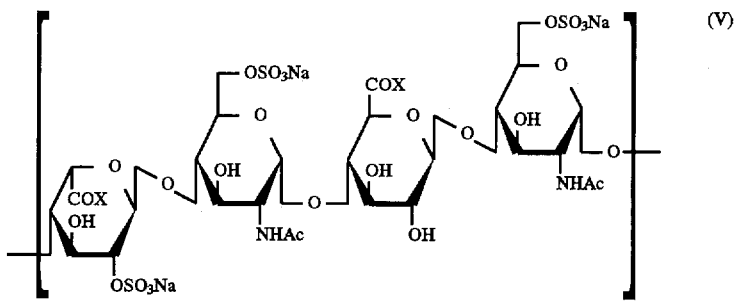

wherein X represents a peptide chain containing 1–8 amino acids, which may be the same or different, and a part or all of the amino groups in the peptide chain which are not involved in the linkages with the N-acetyl-de-N-sulfated heparin or the carboxyl groups in the peptide chain may form an acid amide linkage or an ester linkage with a carboxyl group, an amino group or a hydroxyl group of a third compound having the carboxyl group, the amino group or the hydroxyl group.

The heparin derivative has preferably a molecular weight of the heparin moiety in the range from $2 \times 10^3$ to $6 \times 10^4$, more preferably from $1 \times 10^4$ to $6 \times 10^4$.

In the heparin derivative, the peptide chain is introduced preferably in a proportion from 0.01 to 2.0, more preferably from 0.01 to 0.1 per repeating unit.

The polysaccharide derivative in which the polysaccharide is hyaluronic acid (referred to hereinafter as "the hyaluronic acid derivative") comprises the repeating unit represented by the formula (VI):

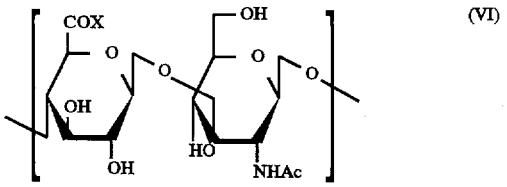

wherein X represents a peptide chain as defined in the formula (V).

The hyaluronic acid derivative has preferably a molecular weight of the hyaluronic acid moiety in the range from $2 \times 10^3$ to $6 \times 10^6$, more preferably from $1 \times 10^4$ to $2 \times 10^5$.

In the hyaluronic acid derivative, the peptide chain is introduced preferably in a proportion from 0.001 to 0.1, more preferably from 0.01 to 0.1 per repeating unit.

Preparation of the Polysaccharide Derivatives

The polysaccharides modified with a carboxyalkyl group can be prepared by replacing the hydrogen atom of the hydroxyl group in the polysaccharide with a carboxyalkyl group. Specifically, it can be prepared by dissolving a polysaccharide in an inert solvent such as $H_2O$, N,N-dimethylformamide or dimethylsulfoxide in the presence of an alkali such as sodium hydroxide or potassium hydroxide, then adding a halogenated acetic acid such as chloroacetic acid, and subjecting to reaction at a temperature from 4° to 100° C. over a period of several minutes to several days. In this reaction, "the degree of substitution" can be controlled by changing the temperature as well as the amount of the chloroacetic acid and the alkali.

The polysaccharide modified with a polybasic acid can be prepared by introducing the polybasic acid into a hydroxyl group in the polysaccharide. Specifically, it can be prepared, for example, by subjecting the polysaccharide to reaction in an inert solvent such as $H_2O$, N,N-dimethylformamide or dimethylsulfoxide (in the presence of a base such as sodium hydrogen carbonate, potassium carbonate, sodium carbonate or aqueous ammonia when water is used as a solvent, or in the presence of pyridine, triethylamine or aminoacetic acid when N,N-dimethylformamide or dimethylsulfoxide is used as a solvent) at a temperature from ice-cooling to 80° C. over a period of several minutes to several days. In this reaction, "the substitution degree" can be controlled by changing the temperature as well as the amount of the alkali.

The polysaccharide derivative according to the present invention can be prepared by introducing a peptide into the carboxyl groups of the polysaccharide. Specifically, when the carboxyl group of the polysaccharide is linked to the N-terminal of a peptide chain through an acid amide linkage, the polysaccharide derivative according to the present invention can be prepared by reacting the polysaccharide with the peptide chain of which the C-terminal has been protected in an inert solvent at a temperature from −20°–40° C. for a period of several minutes to several days. In this reaction, an appropriate condensation agent such as N,N'-dicyclohexylcarbodiimide, 1-ethyl-3-(3-dimthylaminopropyl)-carbodiimide hydrochloride or 1-ethoxycarbonyl-2-ethoxy-1,2-dihydroquinoline is preferably added to the reaction mixture. The reaction may also be carried out optionally by converting the carboxyl group of the polysaccharide into an active ester such as the N-hydroxysuccinimide.

The degree of introducing the peptide chain into the polysaccharide can be adjusted by controlling the amount of the peptide to be added. Therefore, when the peptide chain is intended to be introduced into all of the carboxyl groups, an excessive amount of the peptide is preferably added for reaction.

The drug complex can be prepared by introducing a drug into the peptide of the polysaccharide derivative obtained as above through the linkage between the functional groups of the peptide and the drug.

The drug complex can also be prepared by introducing a peptide chain to which the drug has been preliminarily linked into a polysaccharide.

The drug can be introduced into the peptide chain by reacting the carboxyl group or the amino group of the peptide chain with the functional group or the activated substituent of the drug. For instance, when the drug is intended to be introduced into the C-terminal of the peptide, the drug containing an amino group is introduced into the C-terminal by an acid amide linkage. The reaction can be performed optionally by reacting the peptide which has been converted into an active ester such as N-hydroxysuccinimide with the drug under the condition for forming the acid amide linkage. The drug can also be introduced into the C-terminal by forming an ester linkage between the C-terminal and a drug having an alcoholic hydroxyl group. Furthermore, when the drug is intended to be introduced into the N-terminal of the peptide, the drug having a carboxyl group can also be introduced into the N-terminal by an acid amide linkage.

Furthermore, the polysaccharide derivative according to the present invention may also be prepared by preliminarily obtaining a drug to which a peptide chain has been introduced and next introducing the drug into the polysaccharide. This can appropriately be carried out depending on the properties of functional groups to be used for the reaction in the similar way to the above introduction of the drug into the polysaccharide derivative. When the drug and the peptide chain are reacted, the N-terminal or the C-terminal of the peptide chain which is not involved in the reaction is preferably protected with a protective group.

In the present invention, it is also possible to use a polysaccharide in which the hydroxyl groups have been partly etherated with polyethylene glycol. It is also possible to use a product having any molecular weight which is prepared by the enzymatic decomposition of the polysaccharide.

EXAMPLES

The present invention is now explained in detail with reference to the following examples, but it should not be construed to be limited thereto.

The compound numbers in examples correspond to those shown in the schemes illustrating the synthetic processes below.

The degree of the carboxymethylation or succinylation of the polysaccharide derivative was determined by the alkali titration method. The amount of a drug content (% by weight) was determined on the basis of the absorption analysis with use of the characteristic absorption of a drug (around 478 nm). Gel filtration was carried out under the following conditions:

Column: TSK gel G4000 PW$_{XL}$; Eluent: 0.1M NaCl; Flow rate: 0.8 ml/min.; Column temperature: 40° C.; Amount of sample to be injected: ca. 50 μg.

The following abbreviations are used in Preparations and Examples:

DXR: doxorubicin; DNR: daunorubicin; Trt: triphenylmethyl group (trityl group).

PREPARATION 1

Sodium Carboxymethylpulullan (2)

Pulullan (1) (10 g, weight average molecular weight: ca. 150,000, manufactured by K. K. Hayashibara-seibutsu-kagaku Kenkyujo) was dissolved in a 6N sodium hydroxide solution (140 ml). Chloroacetic acid (30 g) was then added. After the mixture was stirred at 70° C. for 2 hours, methanol (1,000 ml) was added. The mixture was then centrifuged to give precipitates that were then dissolved in purified water (100 ml) to dialyze the solution through a dialyzing membrane (molecular cut-off: 12,000–14,000, manufactured by SPECTRUM CO.) with purified water as an outer solution at 4° C. for 2 days. The dialyzed internal solution was taken out and lyophilized to give the title compound (2) (8.7 g). The product had a degree of carboxymethylation of 0.6 per sugar residue.

PREPARATION 2

Sodium Carboxymethylpulullan (3)

Pulullan (1) (5 g, weight average molecular weight: ca. 150,000, manufactured by K. K. Hayashibara-seibutsu-kagaku Kenkyujo) was dissolved in a 1N sodium hydroxide solution (250 ml). Chloroacetic acid (7.5 g) was next added. After the mixture was stirred at 70° C. for 2 hours, methanol (1,000 ml) was added. The mixture was centrifuged to give precipitates that were then dissolved in purified water (100 ml) to dialyze the solution through a dialyzing membrane (molecular cut-off: 12,000–14,000, manufactured by SPECTRUM CO.) with purified water as an outer solution at 4° C. for 2 days. The dialyzed internal solution was taken out and lyophilized to give the title compound (3) (2.9 g). The product had a degree of carboxymethylation of 0.2 per sugar residue.

PREPARATION 3

Sodium Carboxymethylpulullan (4)

Pulullan (1) (10 g, weight average molecular weight: ca. 150,000, manufactured by K. K. Hayashibara-seibutsu-kagaku Kenkyujo) was dissolved in a 6N sodium hydroxide solution (140 ml). Chloroacetic acid (30 g) was then added. After the mixture was stirred at 70° C. for 2 hours, methanol (1,000 ml) was added. The mixture was centrifuged to give precipitates that were then dried under reduced pressure. The similar operation was conducted twice. The product was dissolved in water (100 ml) to dialyze the solution through a dialyzing membrane (molecular cut-off: 12,000–14,000, manufactured by SPECTRUM CO.) with purified water as an outer solution at 4° C. for 2 days. The dialyzed internal solution was taken out and lyophilized to give the title compound (4) (4.9 g). The product had a degree of carboxymethylation of 1.2 per sugar residue.

PREPARATION 4

Sodium Carboxymethylpulullan (6)

Pulullan (5) (0.5 g, weight average molecular weight: ca. 400,000, manufactured by K. K. Hayashibara-seibutsu-kagaku Kenkyujo) was dissolved in a 1N sodium hydroxide solution (25 ml). Chloroacetic acid (0.75 g) was then added. After the mixture was stirred at 70° C. for 2 hours, methanol (1,000 ml) was added. The mixture was centrifuged to give precipitates that were then dissolved in purified water (10 ml) to dialyze the solution through a dialyzing membrane (molecular cut-off: 12,000–14,000, manufactured by SPECTRUM CO.) with purified water as an outer solution at 4° C. for 2 days. The dialyzed internal solution was taken out and lyophilized to give the title compound (6) (0.45 g). The product had a degree of carboxymethylation of 0.2 per sugar residue.

PREPARATION 5

Sodium Carboxymethylpulullan (8)

Pulullan (7) (0.5 g, weight average molecular weight: ca. 23,000, manufactured by K. K. Hayashibara-seibutsu-kagaku Kenkyujo) was dissolved in a 6N sodium hydroxide solution (7 ml). Chloroacetic acid (1.5 g) was then added. After the mixture was stirred at 70° C. for 2 hours, methanol (100 ml) was added. The mixture was centrifuged to give precipitates that were then dried under reduced pressure. The similar operation was conducted again. The product was dissolved in purified water (10 ml) to dialyze the solution through a dialyzing membrane (molecular cut-off: 1,000, manufactured by SPECTRUM CO.) against purified water as an outer solution at 4° C. for 2 days. The dialyzed internal solution was taken out and lyophilized to give the title compound (8) (0.4 g). The product had a degree of carboxymethylation of 1.0 per sugar residue.

PREPARATION 6

3'-N-(Gly-Gly-Phe-Gly)-DXR·HCl (10)

A solution of $N^\alpha$-Trt-Gly-Gly-Phe-Gly (9) (475 mg, 0.82 mmole) and N-hydroxysuccinimide (115 mg, 1.0 mmole) in N,N-dimethylformamide (4 ml) was cooled to 4° C. After N,N'-dicyclohexylcarbodiimide (206 mg, 1.0 mmole) was added, the mixture was stirred at 4° C. for 2 hours. To this solution was added a solution of DXR (446 mg, 0.82 mmole) in N,N-dimethylformamide (3 ml). The mixture was then stirred at 4° C. for 10 hours. After water (30 ml) was added to the reaction, the mixture was extracted with chloroform (100ml×3). The organic layer was dried with sodium sulfate, concentrated and purified by silica gel chromatography (2.5 cm×40 cm; chloroform:methanol=20:1) to give 3'-N-($N^\alpha$-Trt-Gly-Gly-Phe-Gly)-DXR (766 mg). The product (750 mg) was dissolved in 75% acetic acid (3 ml). The solution was stirred at room temperature for 1 hour. After water (50 ml) was added to the reaction and the precipitates were removed by filtration, the aqueous layer was lyophilized. The lyophilized product was dissolved in purified water (10 ml) and flown through a column of 5 ml of an anion exchange resin (AG1-X8 (Cl⁻ type), BIO-RAD). The aqueous layer was lyophilized to give the title compound (10) (462 mg).

$^1$H-n.m.r. (CD$_3$OD): δ 7.91 (d, 1H, J=7.6 Hz, H-1), 7.80 (t, 1H, H-2), 7.54 (d, 1H, J=8.3 Hz, H-3), 7.16–7.26 (m, 5H, Phe-aromatic), 5.43 (d, 1H, J=3.9 Hz, H-1'), 5.13 (bs, 1H, H-7), 4.73 (s, 2H, H-14), 4.43 (dd, 1H, J=8.4, 6.6 Hz, Phe-α-CH), 4.30 (q, 1H, J=6.6 Hz, H-5'), 4.16 (ddd, 1H, H-3'), 4.03 (d, 1H, J=17.0 Hz, 1H, Gly-α-CHa), 4.02 (s, 3H, 4-OCH$_3$), 3.86 (d, 1H, J=16.9 Hz, Gly-α-CHa), 3.83 (d, 1H, J=17.0 Hz, Gly-α-CHb), 3.77 (d, 1H, J=15.9 Hz, Gly-α-CHa), 3.73 (d, 1H, J=15.9 Hz, Gly-α-CHb), 3.62 (d, 1H, J=1.5 Hz, H-4'), 3.59 (d, 1H, J=16.9 Hz, Gly-α-CHb), 3.13 (dd, 1H, J=13.9, 6.6 Hz, Phe-β-CHa), 3.10 (d, 1H, J=18.6 Hz, H-10a), 3.00 (d, 1H, J=18.6 Hz, H-10b), 2.94 (dd, 1H, J=13.9, 8.4 Hz, Phe-β-CHb), 2.38 (d, 1H, J=14.7 Hz, H-8a), 2.19 (dd, 1H, J=14.7, 5.1 Hz, H-8b), 1.98 (ddd, 1H, J=12.7, 12.7, 3.9 Hz, H-2'a), 1.71 (dd, 1H, J=12.7, 4.6 Hz, H-2'b), 1.28 (d, 3H, J=6.6 Hz, H-6').

PREPARATION 7

3'-N-(Gly-Phe-Gly-Gly)-DXR·HCl (12)

In the same manner as in Preparation 6, to a solution of $N^\alpha$-Trt-Gly-Phe-Gly-Gly (11) (579 mg, 1.0 mmole) and N-hydroxysuccinimide (127 mg, 1.1 mmole) in N,N-dimethylformamide (4 ml) was added N,N'-dicyclohexylcarbodiimide (226 mg, 1.1 mmole) followed by a solution of DXR (544 mg, 1.0 mmole) in N,N-dimethylformamide (3 ml) to give 3'-N-($N^\alpha$-Trt-Gly-Phe-Gly-Gly)-DXR (670 mg). The compound (595 mg) was treated with 75% acetic acid (3 ml) to give the des-N-tritylated product, which was further converted into the hydrochloride as the title compound (12) (316 mg).

$^1$H-n.m.r. (CD$_3$OD): δ 7.97 (d, 1H, J=7.3 Hz, H-1), 7.84 (t, 1H, H-2), 7.57 (d, 1H, J=8.3 Hz, H-3), 7.18–7.28 (m, 5H, Phe-aromatic), 5.44 (d, 1H, J=3.4 Hz, H-1'), 5.17 (bs, 1H, H-7), 4.75 (d, 1H, J=20.8 Hz, H-14a), 4.70 (d, 1H, J=20.8 Hz, H-14b), 4.59 (dd, 1H, J=8.4, 6.0 Hz, Phe-α-CH), 4.28 (q, 1H, J=6.6 Hz, H-5'), 4.14 (ddd, 1H, H-3'), 4.03 (s, 3H, 4-OCH$_3$), 3.85 (d, 1H, J=16.6 Hz, 1H, Gly-α-CHa), 3.84 (d, 1H, J=16.1 Hz, Gly-α-CHa), 3.79 (d, 1H, J=16.6 Hz, Gly-α-CHb), 3.69 (d, 1H, J=16.1 Hz, Gly-α-CHb), 3.68 (d, 1H, J=16.1 Hz, Gly-α-CHa), 3.62 (d, 1H, J=1.5 Hz, H-4'), 3.56 (d, 1H, J=16.1 Hz, Gly-α-CHb), 3.12 (dd, 1H, J=14.0, 6.0 Hz, Phe-β-CHa), 3.12 (d, 1H, J=18.5 Hz, H-10a), 3.04 (d, 1H, J=18.5 Hz, H-10b), 2.94 (dd, 1H, J=14.0, 8.4 Hz, Phe-β-CHb), 2.38 (d, 1H, J=14.7 Hz, H-8a), 2.19 (dd, 1H, J=14.7, 5.1 Hz, H-8b), 2.05 (ddd, 1H, J=12.7, 12.7, 3.4 Hz, H-2'a), 1.71 (dd, 1H, J=12.7, 4.6 Hz, H-2'b), 1.28 (d, 3H, J=6.6 Hz, H-6').

PREPARATION 8

3'-N-(Ala-Leu-Ala-Leu)-DXR·HCl (14)

In the same manner as in Preparation 6, to a solution of $N^\alpha$-Trt-Ala-Leu-Ala-Leu (13) (314 mg, 0.50 mole) and N-hydroxysuccinimide (71 mg, 0.62 mmole) in N,N-dimethylformamide (3 ml) was added N,N'-dicyclohexylcarbodiimide (127 mg, 0.62 mmole) followed by a solution of DXR (272 mg, 0.50 mmole) in N,N-dimethylformamide (3 ml) to give 3'-N-($N^\alpha$-Trt-Ala-Leu-Ala-Leu)-DXR (324 mg). The compound (310 mg) was treated with 75% acetic acid (3 ml) to give the des-N-tritylated product, which was further converted into the hydrochloride as the title compound (14) (217 mg).

$^1$H-n.m.r. (CD$_3$OD): δ 7.95 (d, 1H, J=7.3 Hz, H-1), 7.83 (t, 1H, H-2), 7.57 (d, 1H, J=8.3 Hz, H-3), 5.40 (d, 1H, J=3.2 Hz, H-1'), 5.13 (bs, 1H, H-7), 4.75 (d, 1H, J=20.8 Hz, H-14a), 4.70 (d, 1H, J=20.8 Hz, H-14b), 4.37 (t, 1H, J=7.4 Hz, Leu-α-CH), 4.34 (t, 1H, J=7.3 Hz, Leu-α-CH), 4.28 (q, 1H, J=6.6 Hz, H-5'), 4.26 (q, 1H, J=7.2 Hz, Ala-α-CH), 4.14 (ddd, 1H, H-3'), 4.03 (s, 3H, 4-OCH$_3$), 3.75 (q, 1H, J=7.1 Hz, Ala-α-CH), 3.57 (d, 1H, J=1.5 Hz, H-4'), 3.07 (d, 1H, J=18.0 Hz, H-10a), 2.93 (d, 1H, J=18.0 Hz, H-10b), 2.38 (d, 1H, J=14.7 Hz, H-8a), 2.19 (dd, 1H, J=14.7, 5.1 Hz, H-8b), 2.05 (ddd, 1H, J=12.7, 12.7, 3.2 Hz, H-2'a), 1.71 (dd, 1H, J=12.7, 4.6 Hz, H-2'b), 1.54–1.68 (m, 6H, Leu-β-CH$_2$×2, Leu-γ-CH×2), 1.40 (d, 3H, J=7.1 Hz, Ala-β-CH$_3$), 1.28 (d, 3H, J=6.6 Hz, H-6'), 1.26 (d, 3H, J=7.2 Hz, Ala-β-CH$_3$), 0.87–0.93 (m, 12H, Leu-δ-CH$_3$×4).

PREPARATION 9

3'-N-Gly-DXR·HCl (16)

In the same manner as in preparation 6, to a solution of $N^\alpha$-Trt-Gly (15) (127 mg, 0.40 mmole) and N-hydroxysuccinimide (51 mg, 0.44 mmole) in N,N-dimethylformamide (4 ml) was added N,N'-dicyclohexylcarbodiimide (91 mg, 0.44 mmole) followed by a solution of DXR (220 mg, 0.40 mmole) in N,N-dimethylformamide (3 ml) to give 3'-N-($N^\alpha$-Trt-Gly)-DXR (233 mg). The compound (213 mg) was treated with 75% acetic acid (3 ml) to give the de-N-tritylated product, which was further converted into the hydrochloride as the title compound (16) (148 mg).

$^1$H-n.m.r. (CD$_3$OD): δ 7.93 (d, 1H, J=6.8 Hz, H-1), 7.82 (t, 1H, H-2), 7.55 (d, 1H, J=8.6 Hz, H-3), 5.42 (d, 1H, J=3.4 Hz, H-1'), 5.17 (bs, 1H, H-7), 4.77 (d, 1H, J=20.0 Hz, H-14a), 4.71 (d, 1H, J=20.0 Hz, H-14b), 4.58 (q, 1H, J=6.4 Hz, H-5'), 4.20 (ddd, 1H, H-3'), 4.03 (s, 3H, 4-OCH$_3$), 3.63 (s, 2H, Gly-α-CH$_2$), 3.61 (d, 1H, J=1.5 Hz, H-4'), 3.08 (d, 1H, J=18.7 Hz, H-10a), 2.96 (d, 1H, J=18.7 Hz, H-10b), 2.37 (d, 1H, J=14.4 Hz, H-8a), 2.17 (dd, 1H, J=14.4, 5.1 Hz, H-8b), 2.05 (ddd, 1H, J=12.7, 12.7, 3.4 Hz, H-2'a), 1.75 (dd, 1H, J=12.7, 4.7 Hz, H-2'b), 1.28 (d, 3H, J=6.4 Hz, H-6').

PREPARATION 10

3'-N-(Gly-Phe)-DNR·HCl (18)

In the same manner as in Preparation 6, to a solution of $N^\alpha$-Trt-Gly-Phe (17) (140 mg, 0.30 mmole) and N-hydroxysuccinimide (38 mg, 0.33 mmole) in N,N-dimethylformamide (4 ml) was added N,N'-dicyclohexylcarbodiimide (68 mg, 0.33 mmole) followed by a solution of DNR (159 mg, 0.30 mmole) in N,N-dimethylformamide (3 ml) to give 3'-N-(N$^\alpha$-Trt-Gly-Phe)-DNR (174 mg). The compound (150 mg) was treated with 75% acetic acid (3 ml) to give the des-N-tritylated product, which was further converted into the hydrochloride as the title compound (18) (55 mg).

$^1$H-n.m.r. (CD$_3$OD): δ 7.97 (d, 1H, J=6.8 Hz, H-1), 7.82 (t, 1H, H-2), 7.56 (d, 1H, J=8.3 Hz, H-3), 7.18–7.28 (m, 5H, Phe-aromatic), 5.40 (d, 1H, J=3.4 Hz, H-1'), 5.12 (bs, 1H, H-7), 4.64 (dd, 1H, J=9.0, 5.6 Hz, Phe-α-CH), 4.27 (q, 1H, J=6.6 Hz, H-5'), 4.13 (ddd, 1H, H-3'), 4.03 (s, 3H, 4-OCH$_3$), 3.60 (d, 1H, J=15.9 Hz, Gly-α-CHa), 3.50 (d, 1H, J=15.9 Hz, Gly-α-CHb), 3.44 (d, 1H, J=1.5 Hz, H-4'), 3.10 (dd, 1H, J=13.9, 5.6 Hz, Phe-β-CHa), 3.05 (d, 1H, J=18.5 Hz, H-10a), 3.00 (d, 1H, J=18.5 Hz, H-10b), 2.94 (dd, 1H, J=13.9, 9.0 Hz, Phe-β-CHb), 2.36 (s, 3H, H-14), 2.35 (d, 1H, J=14.4 Hz, H-8a), 2.18 (dd, 1H, J=14.4, 5.1 Hz, H-8b), 1.94 (ddd, 1H, J=13.0, 12.7, 3.4 Hz, H-2'a), 1.69 (dd, 1H, J=13.0, 4.6 Hz, H-2'b), 1.28 (d, 3H, J=6.6 Hz, H-6').

PREPARATION 11

3'-N-(Gly-Gly-Gly-Gly)-DXR·HCl (20)

In the same manner as in Preparation 6, to a solution of N$^\alpha$-Trt-Gly-Gly-Gly-Gly (19) (488 mg, 1.0 mmole) and N-hydroxysuccinimide (127 mg, 1.1 mmole) in N,N-dimethylformamide (5 ml) was added N,N'-dicyclohexylcarbodiimide (227 mg, 1.1 mmole) followed by a solution of DXR (544 mg, 1.0 mmole) in N,N-dimethylformamide (3 ml) to give 3'-N-(N$^\alpha$-Trt-Gly-Gly-Gly-Gly)-DXR (759 mg). The compound (580 mg) was treated with 75% acetic acid (5 ml) to give the de-N-tritylated product, which was further converted into the hydrochloride as the title compound (20) (380 mg).

$^1$H-n.m.r. (CD$_3$OD-D$_2$O): δ 7.87 (d, 1H, J=7.3 Hz, H-1), 7.83 (t, 1H, H-2), 7.55 (d, 1H, J=8.3 Hz, H-3), 5.43 (d, 1H, J=3.4 Hz, H-1'), 5.09 (bs, 1H, H-7), 4.79 (d, 1H, J=21.0 Hz, H-14a), 4.74 (d, 1H, 21.0 Hz, H-14b), 4.28 (q, 1H, J=6.4 Hz, H-5'), 4.16 (ddd, 1H, H-3'), 4.04 (s, 3H, 4-OCH$_3$), 4.03 (d, 1H, J=16.6 Hz, Gly-α-CHa), 3.98 (d, 1H, J=16.6 Hz, Gly-α-CHb), 3.90 (s, 2H, Gly-α-CH$_2$), 3.86 (s, 2H, Gly-α-CH$_2$), 3.81 (s, 2H, Gly-α-CH$_2$), 3.65 (d, 1H, J=1.5 Hz, H-4'), 3.07 (d, 1H, J=18.6 Hz, H-10a), 3.04 (d, 1H, J=18.6 Hz, H-10b), 2.36 (d, 1H, J=14.7 Hz, H-8a), 2.18 (dd, 1H, J=14.7, 3.4 Hz, H-8b), 2.03 (ddd, 1H, J=12.7, 12.7, 3.4 Hz, H-2'a), 1.75 (dd, 1H, J=12.7, 3.9 Hz, H-Cha'b), 1.29 (d, 3H, J=6.4 Hz, H-6').

PREPARATION 12

3'-N-(Gly-Leu-Phe-Gly) -DXR·HCl (22)

In the same manner as in Preparation 6, to solution of N$^\alpha$-Trt-Gly-Leu-Phe-Gly (21) (552 mg, 0.87 mmole) and N-hydroxysuccinimide (115 mg, 1.0 mmole) in N,N-dimethylformamide (5 ml) was added N,N'-dicyclohexylcarbodiimide (206 mg, 1.0 mmole) followed by a solution of DXR (472 mg, 0.87 mmole) in N,N-dimethylformamide (3 ml) to give 3'-N-(N$^\alpha$-Trt-Gly-Leu-Phe-Gly)-DXR (242 mg). The compound (169 mg) was treated with 75% acetic acid (3 ml) to give the de-N-tritylated product, which was further converted into the hydrochloride as the title compound (22) (79 mg).

$^1$H-n.m.r. (CD$_3$OD): δ 7.95 (d, 1H, J=7.8 Hz, H-1), 7.82 (t, 1H, H-2), 7.56 (d, 1H, J=8.6 Hz, H-3), 7.15–7.25 (m, 5H, Phe-aromatic), 5.43 (d, 1H, J=3.9 Hz, H-1'), 5.14 (bs, 1H, H-7), 4.76 (d, 2H, J=20.0 Hz, H-14a), 4.71 (d, 1H, 20.0 Hz, H-14b), 4.44 (dd, 1H, J=9.0, 6.4 Hz, Phe-α-CH), 4.30 (q, 1H, J=6.6 Hz, H-5'), 4.30 (t, 1H, J=7.3 Hz, Leu-α-CH), 4.15 (ddd, 1H, H-3'), 4.03 (s, 3H, 4-OCH$_3$), 3.90 (d, 1H, J=16.9 Hz, Gly-α-CHa), 3.74 (d, 1H, J=15.9 Hz, Gly-α-CHa), 3.70 (d, 1H, J=15.9 Hz, Gly-α-CHb), 3.62 (d, 1H, J=1.5 Hz, H-4'), 3.61 (d, 1H, J=16.9 Hz, Gly-α-CHb), 3.15 (dd, 1H, J=13.9, 6.4 Hz, Phe-β-CHa), 3.10 (d, 1H, J=18.7 Hz, H-10a), 3.01 (d, 1H, J=18.7 Hz, H-10b), 2.96 (dd, 1H, J=13.9, 9.0 Hz, Phe-β-CHb), 2.37 (d, 1H, J=14.7 Hz, H-8a), 2.19 (dd, 1H, J=14.7, 5.1 Hz, H-8b), 2.04 (ddd, 1H, J=12.7, 12.5, 3.9 Hz, H-2'a), 1.71 (dd, 1H, J=12.5, 4.2 Hz, H-2'b), 1.55 (m, 1H, Leu-γ-CH), 1.43 (m, 2H, Leu-β-CH$_2$), 1.29 (d, 3H, J=6.6 Hz, H-6'), 0.89 (d, 3H, J=6.6 Hz, Leu-δ-CH$_3$), 0.85 (d, 3H, J=6.6 Hz, Leu-δ-CH$_3$).

EXAMPLE 1

Sodium Carboxymethylpulullan-3'-N-(Gly-Gly-Phe-Gly)-DXR (23)

Figure 2:
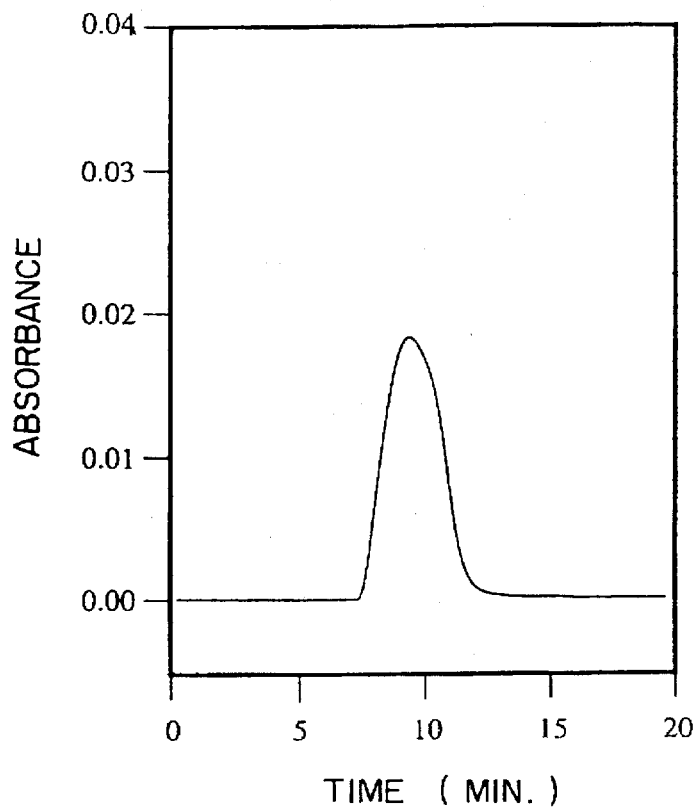
FIG. 2 illustrates an elution pattern by gel filtration of sodium carboxymethylpullulan-3'-N-(Gly-Gly-Phe-Gly)-DXR (23) obtained in Example 1 (detected by visible absorption at 478 nm)

Sodium carboxymethylpulullan (2) (1,000 mg) was dissolved in a mixture of water:N,N-dimethylformamide (1:1) (30 ml). To this solution were added a solution of 3'-N-(Gly-Gly-Phe-Gly)-DXR·HCl (10) (220 mg) in a mixture of water:N,N-dimethyl-formamide (1:1) (6 ml) and 1-ethoxycarbonyl-2-ethoxy-1,2-dihydroquinoline (1,000 mg). The mixture was stirred at room temperature for 2 hours and then subjected to dialysis through a dialysis membrane (molecular cut-off: 12,000–14,000; SPECTRUM CO.) with purified water as an outer solution at 4° C. for 2 days, flown through 50 ml of a cation exchange resin (AG 50W-X8 (N$^+$ type); BIO-RAD), and further subjected to dialysis against purified water at 4° C. for 2 days. The dialyzed internal solution was taken out and lyophilized to give the title compound (23) (1,085 mg). The complex had a drug content of 6.1% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 1 and 2, respectively.

EXAMPLE 2

Sodium Carboxymethylpulullan-3'-N-(Gly-Gly-Phe-Gly)-DXR (24)

Figure 3:
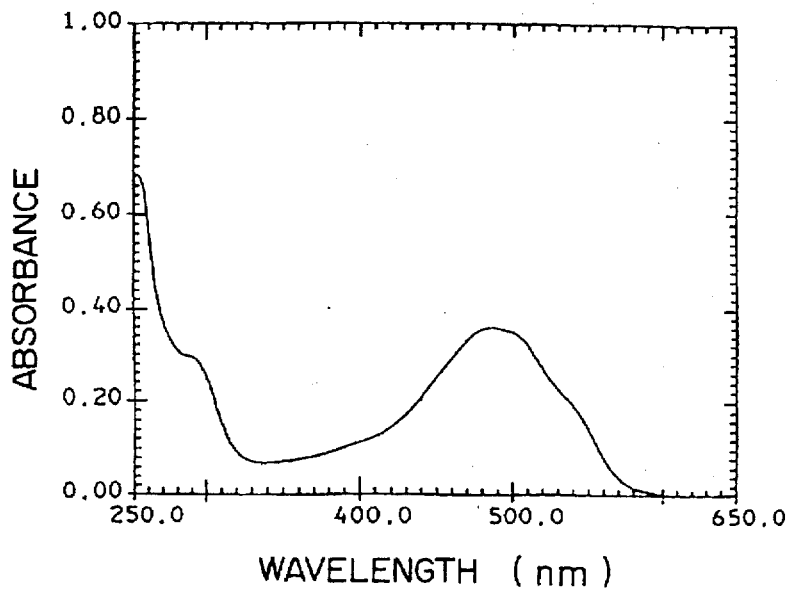
FIG. 3 illustrates an ultraviolet-visible absorption spectrum of sodium carboxymethylpullulan-3'-N-(Gly-Gly-Phe-Gly)-DXR (24) obtained in Example 2 (concentration: 300 µg/ml, solvent: water)
Figure 4:
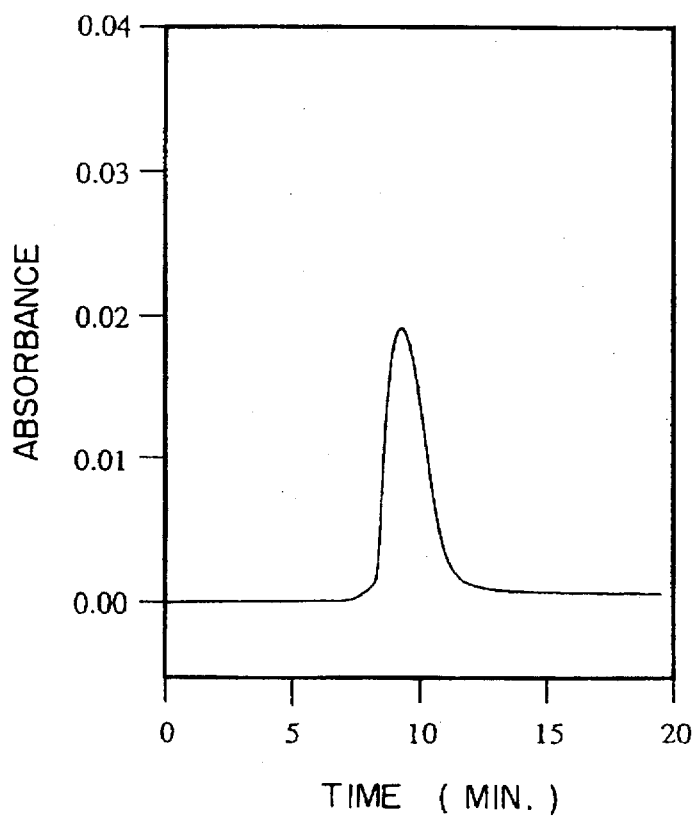
FIG. 4 illustrates an elution pattern by gel filtration of sodium carboxymethylpullulan-3'-N-(Gly-Gly-Phe-Gly)-DXR (24) obtained in Example 2 (detected by visible absorption at 478 nm)

In the same manner as in Example 1, a solution of sodium carboxymethylpulullan (3) (450 mg) in a mixture of water:N,N-dimethylformamide (1:1) (13.5 ml), a solution of 3'-N-(Gly-Gly-Phe-Gly)-DXR·Hcl (10) (100 mg) in a mixture of water:N,N-dimethylformamide (1:1) (4.5 ml) and 1-ethoxycarbonyl-2-ethoxy-1,2-dihydroquinoline (450 mg) were reacted to give the title compound (24) (420 mg). The complex had a drug content of 5.8% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 3 and 4, respectively.

EXAMPLE 3

Sodium Carboxymethylpulullan-3'-N-(Gly-Gly-Phe-Gly)-DXR (25)

In the same manner as in Example 1, a solution of sodium carboxymethylpulullan (4) (600 mg) in a mixture of water:N,N-dimethylformamide (1:1) (18 ml), a solution of 3'-N-(Gly-Gly-Phe-Gly)-DXR·HCl (10) (270 mg) in a mixture of water:N,N-dimethylformamide (1:1) (6 ml) and 1-ethoxycarbonyl-2-ethoxy-1,2-dihydroquinoline (600 mg) were reacted to give the title compound (25) (705 mg). The complex had a drug content of 12.4% (% by weight) determined by the visible absorption spectrophotometry at 478 nm and the total weight of the complex.

EXAMPLE 4

Sodium Carboxymethylpulullan-3'-N-(Gly-Phe-Gly-Gly)-DXR (26)

In the same manner as in Example 1, a solution of sodium carboxymethylpulullan (2) (1,000 mg) in a mixture of water:N,N-dimethylformamide (1:1) (30 ml), a solution of 3'-N-(Gly-Phe-Gly-Gly)-DXR·HCl (12) (220 mg) in a mixture of water:N,N-dimethylformamide (1:1) (10 ml) and 1-ethoxycarbonyl-2-ethoxy-1,2-dihydroquinoline (1,000 mg) were reacted to give the title compound (26) (1,070 mg). The complex had a drug content of 6.1% (% by weight) determined by the visible absorption spectrophotometry at 478 nm and the total weight of the complex.

EXAMPLE 5

Sodium Carboxymethylpulullan-3'-N-(Ala-Leu-Ala-Leu)-DXR (27)

In the same manner as in Example 1, a solution of sodium carboxymethylpulullan (2) (750 mg) in a mixture of water:N,N-dimethylformamide (1:1) (22 ml), a solution of 3'-N-(Ala-Leu-Ala-Leu)-DXR·HCl (14) (180 mg) in a mixture of water:N,N-dimethylformamide (1:1) (8 ml) and 1-ethoxycarbonyl-2-ethoxy-1,2-dihydroquinoline (750 mg) were reacted to give the title compound (27) (856 mg). The complex had a drug content of 6.7% (% by weight) determined by the visible absorption spectrophotometry at 478 nm and the total weight of the complex.

EXAMPLE 6

Sodium Carboxymethylpulullan-3'-N-Gly-DXR (28)

In the same manner as in Example 1, a solution of sodium carboxymethylpulullan (6) (200 mg) in a mixture of water:N,N-dimethylformamide (1:1) (6 ml), a solution of 3'-N-Gly-DXR·HCl (16) (15 mg) in a mixture of water:N,N-dimethylformamide (1:1) (2 ml) and 1-ethoxycarbonyl-2-ethoxy-1,2-dihydroquinoline (100 mg) were reacted to give the title compound (28) (155 mg). The complex had a drug content of 3.1% (% by weight) determined by the visible absorption spectrophotometry at 478 nm and the total weight of the complex.

EXAMPLE 7

Sodium Carboxymethylpulullan-3'-N-Gly-DXR (29)

Figure 5:
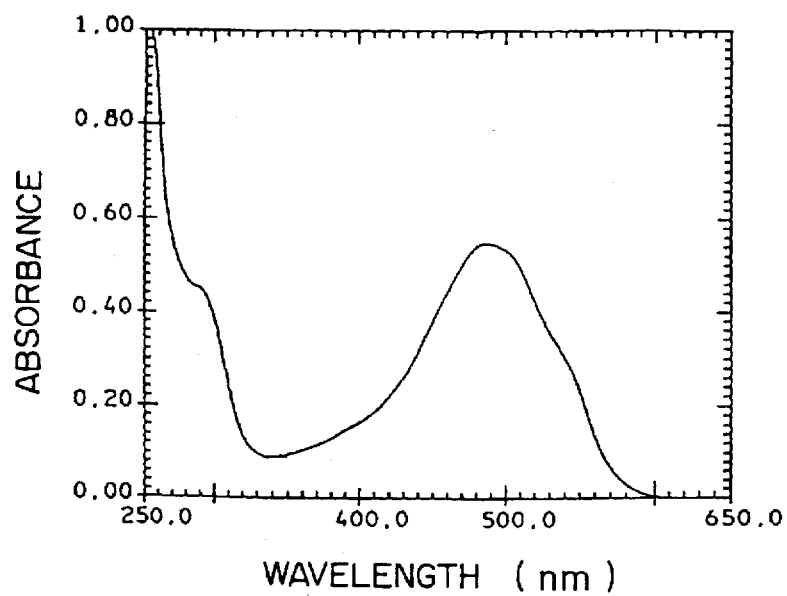
FIG. 5 illustrates an ultraviolet-visible absorption spectrum of sodium carboxymethylpullulan-3'-N-Gly-DXR (29) obtained in Example 7 (concentration: 200 µg/ml, solvent: water)
Figure 6:
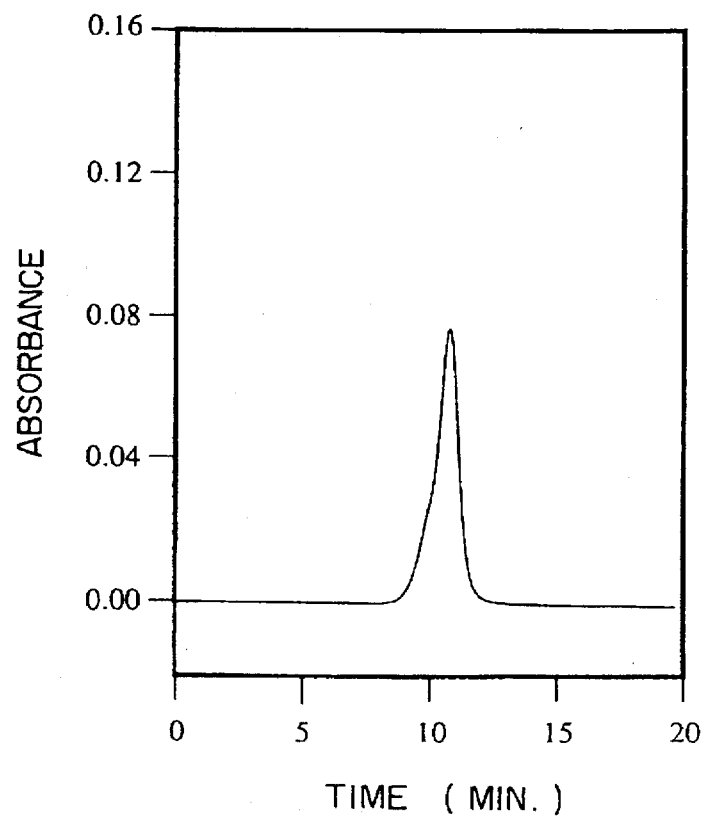
FIG. 6 illustrates an elution pattern by gel filtration of sodium carboxymethylpullulan-3'-N-Gly-DXR (29) obtained in Example 7 (detected by visible absorption at 478 nm)

In the same manner as in Example 1 except that a dialysis membrane having ammolecular weight cut-off of 1,000 was used as the dialysis membrane, a solution of sodium carboxymethylpulullan (8) (100 mg) in a mixture of water:N,N-dimethylformamide (1:1) (3 ml), a solution of 3'-N-Gly-DXR·HCl (16) (40 mg) in a mixture of water:N,N-dimethylformamide (1:1) (2 ml) and 1-ethoxycarbonyl-2-ethoxy-1,2-dihydroquinoline (100 mg) were reacted to give the title compound (29) (111 mg). The complex had a drug content of 12.6% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 5 and 6, respectively.

EXAMPLE 8

Sodium Carboxymethylpulullan-3'-N-(Gly-Phe)-DNR (30)

In the same manner as in Example 1, a solution of sodium carboxymethylpulullan (2) (200 mg) in a mixture of water:N,N-dimethylformamide (1:1) (6 ml), a solution of 3'-N-(Gly-Phe)-DNR·HCl (18) (32 mg) in a mixture of water:N,N-dimethylformamide (1:1) (2 ml) and 1-ethoxycarbonyl-2-ethoxy-1,2-dihydroquinoline (200 mg) were reacted to give the title compound (30) (185 mg). The complex had a drug content of 5.6% (% by weight) determined by the visible absorption spectrophotometry at 478 nm and the total weight of the complex.

EXAMPLE 9

Sodium Carboxymethylpulullan-3'-N-(Gly-Gly-Gly-Gly)-DXR (31)

In the same manner as in Example 1, a solution of sodium carboxymethylpulullan (2) (300 mg) in a mixture of water:N,N-dimethylformamide (1:1) (9 ml), a solution of 3'-N-(Gly-Gly-Gly-Gly)-DXR·HCl (20) (63 mg) in a mixture of water:N,N-dimethylformamide (1:1) (3 ml) and 1-ethoxycarbonyl-2-ethoxy-1,2-dihydroquinoline (300 mg) were reacted to give the title compound (31) (330 mg). The complex had a drug content of 6.9% (% by weight) determined by the visible absorption spectrophotometry at 478 nm and the total weight of the complex.

EXAMPLE 10

Sodium Carboxymethylpulullan-3'-N-(Gly-Leu-Phe-Gly)-DXR (32)

In the same manner as in Example 1, a solution of sodium carboxymethylpulullan (2) (200 mg) in a mixture of water:N,N-dimethylformamide (1:1) (6 ml), a solution of 3'-N-(Gly-Leu-Phe-Gly)-DXR·HCl (22) (48 mg) in a mixture of water—N,N-dimethylformamide (1:1) (2 ml) and 1-ethoxycarbonyl-2-ethoxy-1,2-dihydroquinoline (200 mg) were reacted to give the title compound (32) (183 mg). The complex had a drug content of 6.2% (% by weight) determined by the visible absorption spectrophotometry at 478 nm and the total weight of the complex.

EXAMPLE 11

Sodium Carboxymethylpulullan-3'-N-(Gly-Gly-Phe-Gly)-DXR (33)

In the same manner as in Example 1, a solution of sodium carboxymethylpulullan (4) (400 mg) in a mixture of water:N,N-dimethylformamide (1:1) (12 ml), a solution of 3'-N-(Gly-Gly-Phe-Gly)-DXR·HCl (10) (88 mg) in a mixture of water:N,N-dimethylformamide (1:1) (4 ml) and 1-ethoxycarbonyl-2-ethoxy-1,2-dihydroquinoline (400 mg) were reacted to give the title compound (33) (348 mg). The complex had a drug content of 7.3% (% by weight) determined by the visible absorption spectrophotometry at 478 nm and the total weight of the complex.

EXAMPLE 12

Sodium Carboxymethylpulullan-3'-N-(Gly-Gly-Phe-Gly)-DXR (34)

In the same manner as in Example 1, a solution of sodium carboxymethylpulullan (2) (200 mg) in a mixture of water:N,N-dimethylformamide (1:1) (6 ml), a solution of 3'-N-(Gly-Gly-Phe-Gly)-DXR·HCl (10) (88 mg) in a mixture of water:N,N-dimethylformamide (1:1) (4 ml) and 1-ethoxycarbonyl-2-ethoxy-1,2-dihydroquinoline (200 mg) were reacted to give the title compound (34) (251 mg). The complex had a drug content of 11.0% (% by weight) determined by the visible absorption spectrophotometry at 478 nm and the total weight of the complex.

PREPARATION 13

3'-N-(Gly)$_6$-DXR·HCl (36)

In the same manner as in Preparation 6, to a solution of N$^\alpha$-Trt-(Gly)$_6$-OH (35) (240 mg, 0.4 mmole) and N-hydroxysuccinimide (57 mg, 0.5 mmole) in N,N-dimethylformamide (4 ml) was added N,N'-dicyclohexylcarbodiimide (103 mg, 0.5 mmole) followed by a solution of DXR (217 mg, 0.4 mmole) in N,N-dimethylformamide (3 ml) to give 3'-N-(N$^\alpha$-Trt-(Gly)$_6$-)-DXR (177 mg). The compound (167 mg) was treated with 75% acetic acid (3 ml) to give the de-N-tritylated product, which was further converted into the hydrochloride as the title compound (36) (98 mg).

$^1$H-n.m.r. (CD$_3$OD-D$_2$O): δ 7.73 (t, 1H, H-2), 7.69 (d, 1H, J=6.6 Hz, H-1), 7.42 (d, 1H, J=8.3 Hz, H-3), 5.41 (bs, 1H, H-1'), 4.98 (bs, 1H, H-7), 4.81 (d, 1H, J=20.3 Hz, H-14a), 4.70 (d, 1H, J=20.0 Hz, H-14b), 4.26 (q, 1H, J=6.6 Hz, H-5'), 4.16 (ddd, 1H, H-3'), 4.02 (s, 2H, Gly-α-CHa), 3.98 (s, 3H, 4-OCH$_3$), 3.96 (s, 4H, Gly-α-CH$_2$×2), 3.92 (s, 2H, Gly-α-CH$_2$), 3.91 (d, 1H, J=17.1 Hz, Gly-α-CH$_2$), 3.87 (d, 1H, J=17.1 Hz, Gly-α-CHb), 3.85 (s, 2H, Gly-α-CH$_2$), 3.68 (d, 1H, J=1.5 Hz, H-4'), 2.98 (d, 1H, J=18.1 Hz, H-10a), 2.76 (d, 1H, J=18.1 Hz, H-10b), 2.34 (d, 1H, J=14.2 Hz, H-8a), 2.13 (dd, 1H, J=13.9, 3.7 Hz, H-8b), 2.03 (ddd, 1H, J=13.2, 13.2, 3.9 Hz, H-2'a), 1.76 (dd, 1H, J=11.9, 3.3 Hz, H-2'b), 1.30 (d, 3H, J=6.6 Hz, H-6').

PREPARATION 14

3'-N-(Phe-Gly)-DXR·HCl (38)

In the same manner as in Preparation 6, to a solution of N$^\alpha$-Trt-(Phe-Gly)-OH (37) (232 mg, 0.5 mmole) and N-hydroxysuccinimide (63 mg, 0.55 mmole) in N,N-dimethylformamide (4 ml) was added N,N'-dicyclohexylcarbodiimide (113 mg, 0.55 mmole) followed by a solution of DXR (272 mg, 0.5 mmole) in N,N-dimethylformamide (3 ml) to give 3'-N-(N$^\alpha$-Trt-Phe-Gly)-DXR (214 mg). The compound (200 mg) was treated with 75% acetic acid (3 ml) to give the de-N-tritylated product, which was further converted into the hydrochloride as the title compound (38) (98 mg).

$^1$H-n.m.r. (CD$_3$OD): δ 7.89 (d, 1H, J=7.3 Hz, H-1), 7.79 (t, 1H, H-2), 7.52 (d, 1H, J=8.3 Hz, H-3), 7.21–7.30 (m, 5H, Phe-aromatic), 5.41 (d, 1H, J=3.7 Hz, H-1'), 5.11 (bs, 1H, H-7), 4.76 (d, 2H, J=19.9 Hz, H-14a), 4.71 (d, 1H, J=19.9 Hz, H-14b), 4.27 (q, 1H, J=6.4 Hz, H-5'), 4.16 (ddd, 1H, H-3'), 4.05 (dd, 1H, J=8.1, 6.4 Hz, Phe-α-CH), 4.02 (s, 3H, 4-OCH$_3$), 3.92 (d, 1H, J=16.5 Hz, Gly-α-CHa), 3.75 (d, 1H, J=16.5 Hz, Gly-α-CHb), 3.60 (d, 1H, J=1.5 Hz, H-4'), 3.18 (dd, 1H, J=14.0, 6.4 Hz, Phe-β-CHa), 3.05 (d, 1H, J=18.7 Hz, H-10a), 2.98 (dd, 1H, J=14.0, 8.1 Hz, Phe-β-CHb), 2.92 (d, 1H, J=18.7 Hz, H-10b), 2.36 (d, 1H, J=14.4 Hz, H-8a), 2.17 (dd, 1H, J=14.4, 4.6 Hz, H-8b), 1.97 (ddd, 1H, J=13.2, 13.2, 3.9 Hz, H-2'a), 1.73 (dd, 1H, J=13.2, 4.6 Hz, H-2'b), 1.27 (d, 3H, J=6.4 Hz, H-6').

EXAMPLE 13

Sodium Carboxymethylpulullan-3'-N-(Gly)$_6$-DXR (39)

In the same manner as in Example 1, a solution of sodium carboxymethylpulullan (2) (300 mg) in a mixture of water:N,N-dimethylformamide (1:1) (9 ml), a solution of 3'-N-(Gly)$_6$-DXR·HCl (36) (66 mg) in a mixture of water:N, N-dimethylformamide (1:1) (6 ml) and 1-ethoxycarbonyl-2-ethoxy-1,2-dihydroquinoline (300 mg) were reacted to give the title compound (39) (327 mg). The complex had a drug content of 6.3% (% by weight) determined by the visible absorption spectrophotometry at 478 nm and the total weight of the complex.

EXAMPLE 14

Sodium Carboxymethylpulullan-3'-N-(Phe-Gly)-DXR (40)

In the same manner as in Example 1, a solution of sodium carboxymethylpulullan (2) (250 mg) in a mixture of water:N,N-dimethylformamide (1:1) (7.5 ml), a solution of 3'-N-(Phe-Gly)-DXR·HCl (38) (45 mg) in a mixture of water:N,N-dimethylformamide (1:1) (2.5 ml) and 1-ethoxycarbonyl-2-ethoxy-1,2-dihydroquinoline (250 mg) were reacted to give the title compound (40) (223 mg). The complex had a drug content of 6.5% (% by weight) determined by the visible absorption spectrophotometry at 478 nm and the total weight of the complex.

PREPARATION 15

Sodium Succinylpulullan (41)

Pulullan (1) (3.2 g, weight average molecular weight: ca. 150,000, manufactured by K. K. Hayashibara-seibutsu-kagaku Kenkyujo) and lithium chloride (2.5 g) were dissolved in N,N-dimethylformamide (30 ml). Succinic anhydride (3.0 g) and N-methylmorpholine (3.03 g) were then added to the solution. After the mixture was stirred at room temperature for 1 hour, methanol (100 ml) was added. The mixture was centrifuged to give precipitates that were then dissolved in water (30 ml). The aqueous solution was flown through 50 ml of a cation exchange resin (AG 50W-X8 (N$^+$ type); BIO-RAD), and further subjected to dialysis against purified water at 4° C. for 2 days. The dialyzed internal solution was then taken out and lyophilized to give the title compound (41) (2.31 g). This product had a degree of succinylation of 0.7 (per sugar residue determined by the alkali titration).

EXAMPLE 15

Sodium Succinylpulullan-3'-N-(Gly-Gly-Phe-Gly)-DXR (42)

Figure 7:
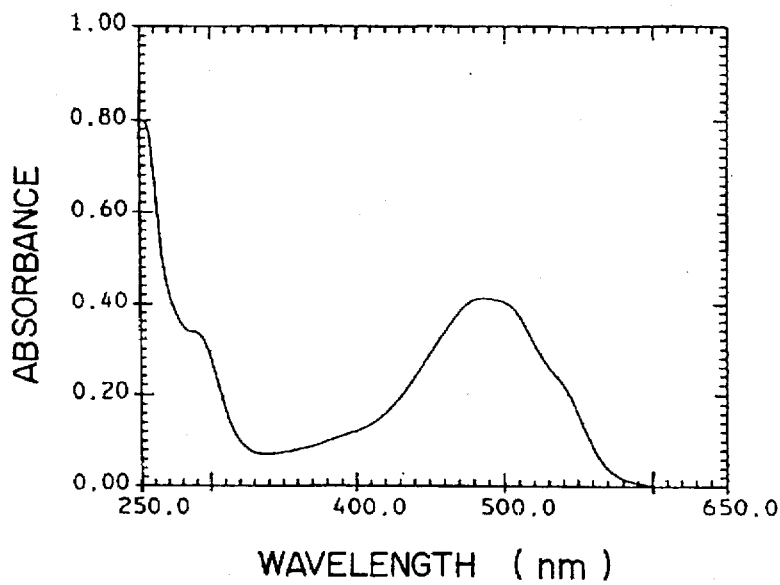
FIG. 7 illustrates an ultraviolet-visible absorption spectrum of sodium succinylpullulan-3'-N-(Gly-Gly-Phe-Gly)-DXR (42) obtained in Example 15 (concentration: 300 µg/ml, solvent: water)
Figure 8:
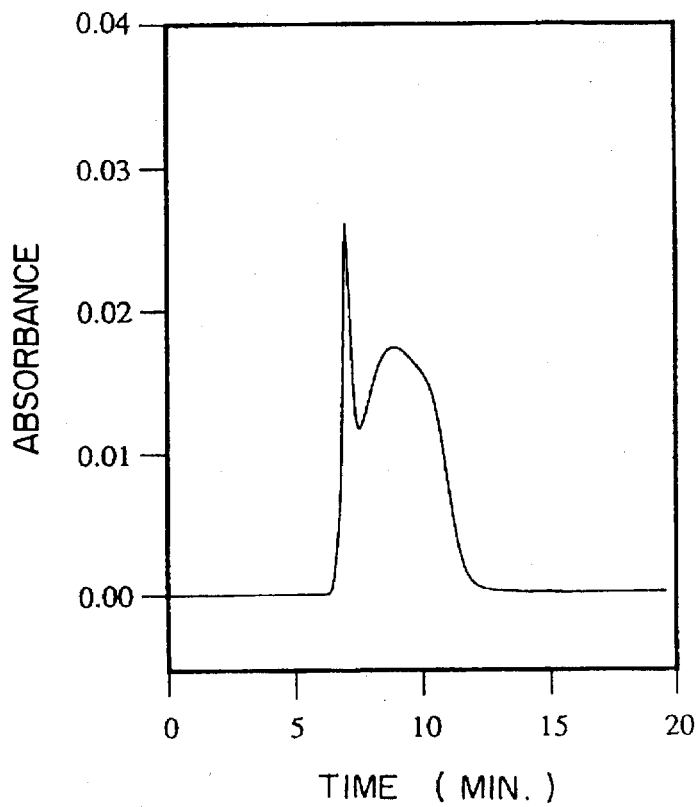
FIG. 8 illustrates an elution pattern by gel filtration of sodium succinylpullulan-3'-N-(Gly-Gly-Phe-Gly)-DXR (42) obtained in Example 15 (detected by visible absorption at 478 nm)

In the same manner as in Example 1, a solution of sodium succinylpulullan (41) (300 mg) in a mixture of water:N,N-dimethylformamide (1:1) (9 ml), a solution of 3'-N-(Gly-Gly-Phe-Gly)-DXR·HCl (10) (66 mg) in a mixture of water:N,N-dimethylformamide (1:1) (3 ml) and 1-ethoxycarbonyl-2-ethoxy-1,2-dihydroquinoline (300 mg) were reacted to give the title compound (42) (327 mg). The complex had a drug content of 6.8% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 7 and 8, respectively.

PREPARATION 16

Sodium a Low-Molecular Weight Carboxymethylchitin (43)

Carboxymethylchitin (degree of carboxymethylation: 0.7; manufactured by Katakura Chikkarin Co.) (20.0 g) was dissolved in a 50 mM sodium acetate solution (pH 6.0) (2.0 liters) and warmed to a temperature of 37° C. A solution of lysozyme (derived from egg white, 51,500 Units/mg of solid; manufactured by Seikagaku Co.) (60 mg) dissolved in purified water was added to this solution. The mixture was stirred at 37° C. for 2.5 hours and added to 99.5% ethanol (1.2 liters). The precipitate thus obtained was washed with 95% ethanol, acetone and ether, and dried under reduced pressure to give a white amorphous product of carboxymethylchitin(17.6 g).

The carboxymethylchitin (17.6 g) was dissolved in purified water (1.2 liters). Sodium borohydride (2.64 g) was added in three portions to the solution. The mixture was stirred overnight at 4° C. After hydrochloric acid was added to the reaction to adjust to pH 4.0, a sodium hydroxide solution was added and the mixture was adjusted to pH 8.1. The solution was passed through a membrane filter (0.3 μm), and the filtrate was added to 99.5% ethanol (10 liters). The resulting precipitate was washed with 95% ethanol, acetone and ether in sequence, and dried under reduced pressure to give sodium carboxymethylchitin (14.4 g) of which the reducing terminal had been reduced.

Next, sodium carboxymethylchitin of which the reducing terminal had been reduced (4.0 g) was dissolved in a 0.2M sodium chloride solution (400 ml). The solution was added to a 240 ml column of an anion exchange resin (AG1-X2 (Cl type); BIO-RAD) which had been preliminarily equilibrated with a 0.2M sodium chloride solution. Elution was then carried out stepwise with various concentrations of aqueous sodium chloride solutions. The eluate with a 0.4M sodium chloride solution was added to 99.5% ethanol (3.5 liters). The precipitates thus obtained were washed with 95% ethanol, acetone and ether in sequence and dried under reduced pressure to give a sodium carboxymethylchitin having a smaller molecular weight (713 mg).

The sodium carboxymethylchitin (600 mg) thus obtained was dissolved in a saturated sodium hydrogen carbonate solution (60 ml). Acetic anhydride (2.4 ml) was added in four portions, and the mixture was stirred overnight at 4° C. The reaction mixture was dialyzed through a dialysis membrane (molecular weight cut-off: 12,000–14,000; SPECTRUM CO.) against purified water as an outer solution at 4° C. for 3 days. The reaction solution was passed through a membrane filter (0.22 μm) and added to 99.5% ethanol (600 ml). The precipitate thus obtained was washed with 95% ethanol, acetone and ether in sequence, dried under reduced pressure to give the title compound (43) (550 mg), which had a molecular weight of about 70,000 based on the gel filtration method with dextran as a standard material.

EXAMPLE 16

Sodium Carboxymethylchitin-3'-N-(Gly-Gly-Phe-Gly)-DXR (44)

Figure 9:
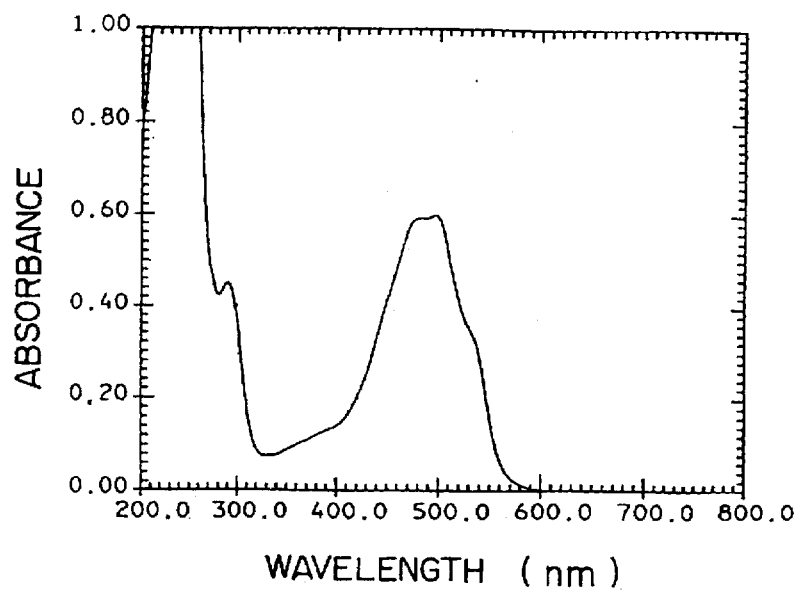
FIG. 9 illustrates an ultraviolet-visible absorption spectrum of sodium carboxymethylchitin-3'-N-(Gly-Gly-Phe-Gly)-DXR (44) obtained in Example 16 (concentration: 1.1 mg/ml, solvent: water)
Figure 10:
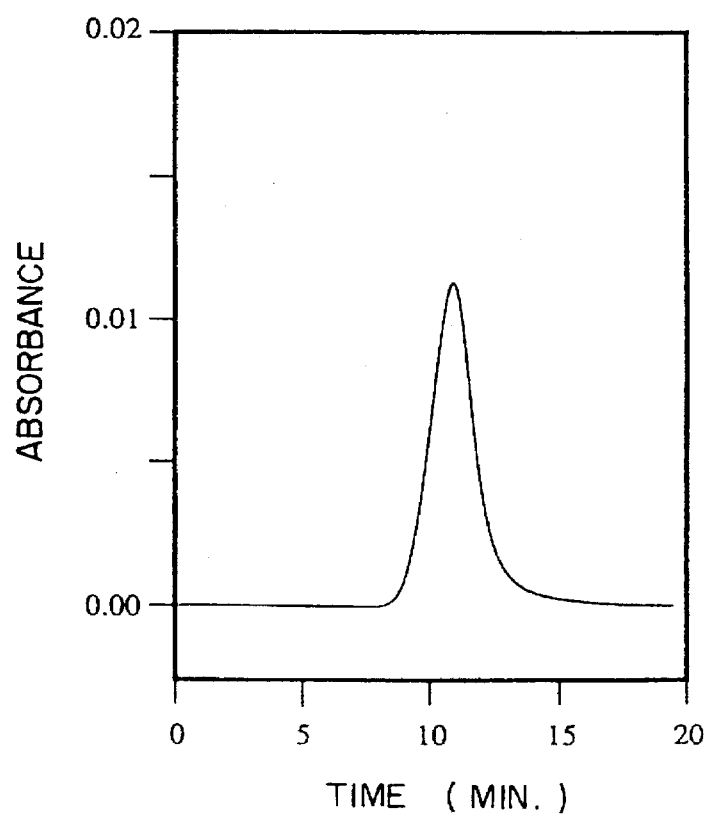
FIG. 10 illustrates an elution pattern by gel filtration of sodium carboxymethylchitin-3'-N-(Gly-Gly-Phe-Gly)-DXR (44) obtained in Example 16 (detected by visible absorption at 478 nm)

In the same manner as in Example 1, a solution of sodium carboxymethylchitosan (43) (100 mg) in a mixture of water:N,N-dimethylformamide (1:1) (3 ml), a solution of 3'-N-(Gly-Gly-Phe-Gly)-DXR·HCl (10) (10.4 mg) in a mixture of water:N,N-dimethylformamide (1:1) (1 ml) and 1-ethoxycarbonyl-2-ethoxy-1,2-dihydroquinoline (100 mg) were reacted to give the title compound (44) (96 mg). The complex had a drug content of 2.7% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 9 and 10, respectively.

PREPARATION 17

Sodium Carboxymethyldextran (45)

Dextran (molecular weight: ca. 70,000; manufactured by Pharmacia) (1.0 g) was dissolved in a 6N sodium hydroxide solution (8.3 ml) and heated to 70° C. Monochloroacetic acid (2.0 g) was added to the solution. The resulting mixture was stirred at 70° C. for 20 minutes. After the reaction solution was ice-cooled, and adjusted to pH 8.5 by the addition of acetic acid. The solution was then added to methanol (500 ml). The precipitate thus obtained was dissolved in purified water (20 ml) and, the solution was dialyzed through a dialysis membrane (molecular weight cut-off: 12,000–14,000; manufactured by SPECTRUM CO.) against purified water as an outer solution at 4° C. for 2 days. The dialyzed internal solution was taken out and lyophilized to give the title compound (45) (0.9 g). This material had a degree of carboxymethylation of 0.6 per sugar residue.

EXAMPLE 17

Sodium Carboxymethyldextran-3'-N-(Gly-Gly-Phe-Gly)-DXR (46)

Figure 11:
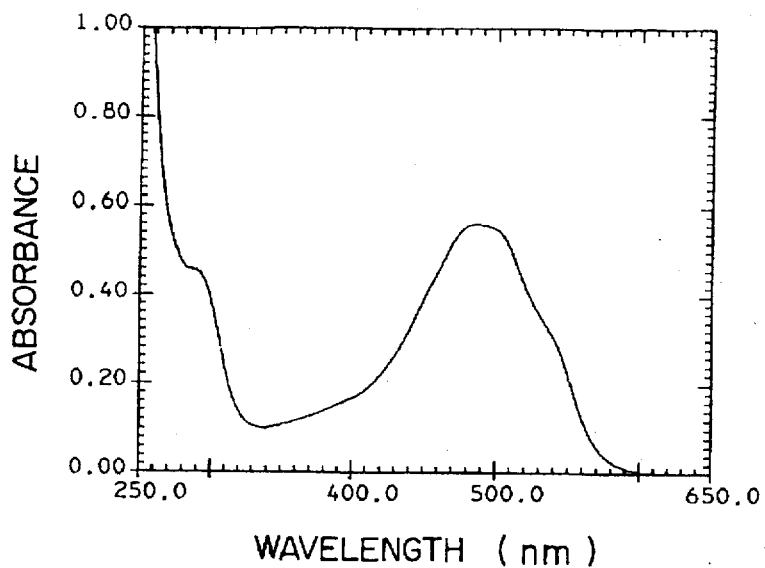
FIG. 11 illustrates an ultraviolet-visible absorption spectrum of sodium carboxymethyldextran-3'-N-(Gly-Gly-Phe-Gly)-DXR (46) obtained in Example 17 (concentration: 400 µg/ml, solvent: water)
Figure 12:
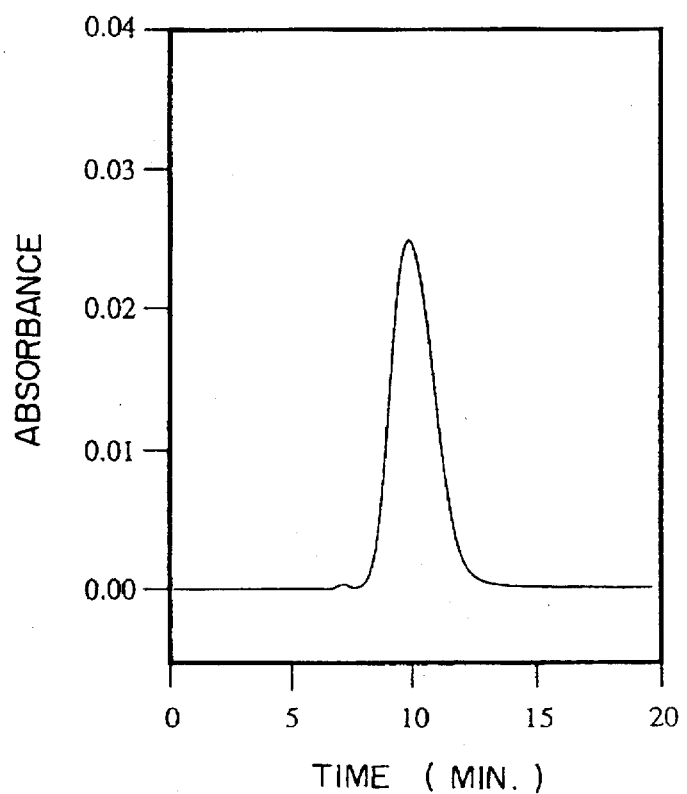
FIG. 12 illustrates an elution pattern by gel filtration of sodium carboxymethyldextran-3'-N-(Gly-Gly-Phe-Gly)-DXR (46) obtained in Example 17 (detected by visible absorption at 478 nm)

In the same manner as in Example 1, a solution of sodium carboxymethyldextran (45) (300 mg) in a mixture of water:N,N-dimethylformamide (1:1) (9 ml), a solution of 3'-N-(Gly-Gly-Phe-Gly)-DXR·HCl (10) (66 mg) in a mixture of water:N,N-dimethylformamide (1:1) (3 ml) and 1-ethoxycarbonyl-2-ethoxy-1,2-dihydroquinoline (300 mg) were reacted to give the title compound (46) (297 mg). The complex had a drug content of 5.7% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 11 and 12, respectively.

PREPARATION 18

Low-Molecular Weight Carboxymethylmannoglucan (47)

Mannoglucan (7.0 g) isolated from a titrate of a culture of Actinomycete *Microellobosporia grisea* was dissolved in 0.1N hydrochloric acid (280 ml). The solution was heated at 80° C. for 7.5 hours. The reaction mixture was adjusted pH 7.0 under ice-cooling with a 5N sodium hydroxide solution and added to 99.5% ethanol (900 ml). The precipitates thus obtained was washed with 95% ethanol and then dissolved in purified water (450 ml). The solution was passed through a 60 ml column of a cation exchange resin (AG50W-X2 (H$^+$ type); BIO-RAD). The eluate was further passed through a 60 ml column of an anion exchange resin (AG1-X2 (Cl$^-$ type); BIO-RAD). The final eluate was concentrated to a volume of 250 ml under reduced pressure and added to 99.5% ethanol (800 ml). The precipitate thus obtained was washed with 95% ethanol, acetone and ether in sequence and dried under reduced pressure to give a low-molecular weight mannoglucan (6.02 g).

The low-molecular weight mannoglucan thus obtained (3.98 g) was dissolved in a 1M sodium chloride solution (400 ml). Methanol (533 ml) was then added to the solution to give the precipitate which was then dissolved in purified water (100 ml). The resulting solution was added to 99.5% ethanol (400 ml). The precipitates thus obtained was washed with 95% ethanol, acetone and ether in sequence and dried under reduced pressure to give a low-molecular weight mannoglucan (2.0 g).

Water (72 ml) and sodium hydroxide (12.6 g) were added to this low-molecular weight mannoglucan (1.80 g) to form a solution. After chloroacetic acid (18.0 g) was added under ice-cooling to this solution, the mixture was stirred at room temperature for 20 hours. The reaction mixture was adjusted to pH 8.0 by the addition of acetic acid and then added to methanol (360 ml). The precipitates thus obtained was washed with methanol, acetone and ether in sequence and dried under reduced pressure to give a low-molecular weight sodium carboxymethylmannoglucan (2.23 g).

The above carboxymethylation was repeated again to give the title compound (2.25 g), which had a molecular weight of about 110,000 determined by the gel filtration method with dextran as a standard material. This compound had a degree of carboxymethylation 0.8 per sugar residue determined by the alkali titration.

EXAMPLE 18

Sodium Carboxymethylmannoglucan-3'-N-(Gly-Gly-Phe-Gly)-DXR (48)

Figure 13:
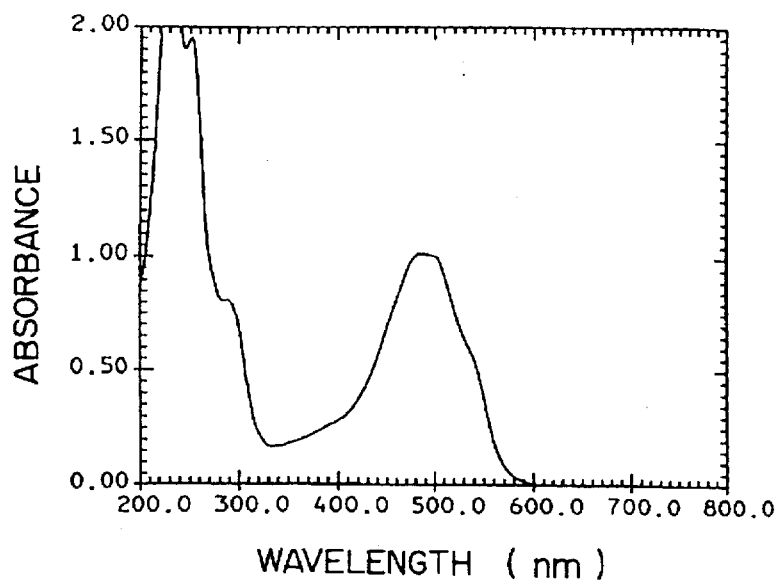
FIG. 13 illustrates an ultraviolet-visible absorption spectrum of sodium carboxymethylmannoglucan-3'-N-(Gly-Gly-Phe-Gly)-DXR (48) obtained in Example 18 (concentration: 1.12 mg/ml, solvent: water)
Figure 14:
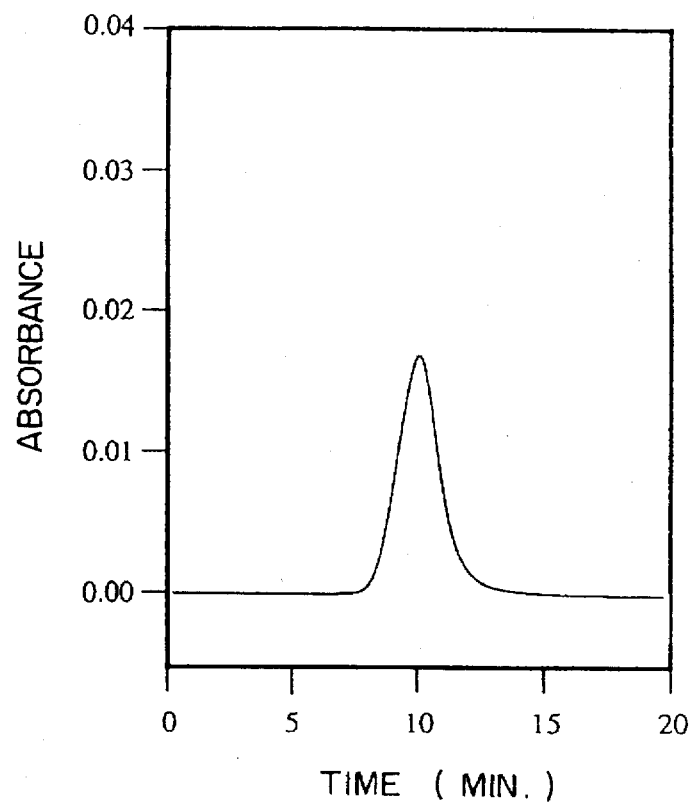
FIG. 14 illustrates an elution pattern by gel filtration of sodium carboxymethylmannoglucan-3'-N-(Gly-Gly-Phe-Gly)-DXR (48) obtained in Example 18 (detected by visible absorption at 478 nm)

In the same manner as in Example 1, a solution of sodium carboxymethylmannoglucan (47) (100 mg) in a mixture of water:N,N-dimethylformamide (1:1) (3 ml), a solution of 3'-N-(Gly-Gly-Phe-Gly)-DXR·HCl (10) (11.9 mg) in a mixture of water:N,N-dimethylformamide (1:1) (1 ml) and 1-ethoxycarbonyl-2-ethoxy-1,2-dihydroquinoline (100 mg) were reacted to give the title compound (48) (99 mg). The complex had a drug content of 4.5% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 13 and 14, respectively.

PREPARATION 19

N-acetyl-de-N-sulfated heparin (49)

Sodium de-N-sulfated heparin (1.0 g, derived from porcine mucosal, manufactured by Sigma Co.) was dissolved in a saturated sodium hydrogen carbonate solution (100 ml). Acetic anhydride (4 ml) was added in four portions with an interval of 15 minutes. After the mixture was stirred overnight at 4° C., the reaction mixture was adjusted to pH 6.5 by the addition of acetic acid and then added to 99.5% ethanol (700 ml). The precipitate thus obtained was dissolved in distilled water (50 ml) and passed through a membrane filter (0.22 µm). The eluate was added to 99.5% ethanol (400 ml). The resulting precipitates were washed with 95% ethanol, acetone and ether in sequence and dried under reduced pressure to give the title compound (900 mg) as a white amorphous product, which had a molecular weight of about 40,000 determined by the gel filtration method with dextran as a standard material.

EXAMPLE 19

Sodium N-acetyl-de-N-sulfated heparin-(Gly-Gly-Phe-Gly)-DXR Complex (50)

A solution of sodium N-acetyl-de-N-sulfated heparin (49) (340 mg) in a mixture of water:N,N-dimethylformamide (1:1) (20 ml), a solution of 3'-N-(Gly-Gly-Phe-Gly)-DXR·HCl (10) (75 mg) in a mixture of water:N,N-dimethylformamide (1:1) (10 ml) and 1-ethoxycarbonyl-2-ethoxy-1,2-dihydroquinoline (340 mg) were stirred at room temperature for 3 hours. The reaction mixture was subjected to dialysis through a dialysis membrane (molecular weight cut-off: 12,000–14,000; manufactured by SPECTRUM CO.) against purified water as an outer solution at 4° C. for 3 days. The dialyzed internal solution was passed through a 20 ml column of a cation exchange resin (AG50W-X8 (Na⁺ type); BIO-RAD) and further passed through a membrane filter (0.45 µm). The eluate was added to 99.5% ethanol (400 ml). The precipitate thus obtained was washed with 95% ethanol, acetone and ether in sequence and dried under reduced pressure. The residue thus obtained was dissolved in purified water (20 ml), passed through a membrane filter (0.45 µm) and lyophilized to give the title compound (50) (328 mg). The complex had a drug content of 4.2% (% by weight) determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 15 and 16, respectively.

PREPARATION 20

Low-Molecular Weight Sodium Hyaluronate (51) (52)

To 110 ml of an intra-articular injection of sodium hyaluronate (derived from roaster comb; weight average molecular weight: 600,000–1,200,000; manufactured by Seikagaku Co. Kaken Pharmaceutical Co.; 25 mg/2.5 ml solution) was added a 1.5M sodium chloride-1M sodium acetate solution (pH 5.0) (11 ml). After the mixture was heated to 37° C., Hyaluronidase (2,200 U) (derived from sheep testes; 2,400 Units/mg solid; manufactured by Sigma Co.) dissolved in ice-cooled purified water was added to the solution. The mixture was then stirred at 37° C. for 2 hours. The reaction mixture was added to 99.5% ethanol (1.4 liters) to give the precipitate, which was then dissolved in 20 ml of distilled water and passed through a membrane filter (0.45 µm). The eluate was added to 99.5% ethanol (200 ml). The precipitate thus obtained was washed with 95% ethanol, acetone and ether in sequence and dried under reduced pressure to give sodium hyaluronate as a while amorphous product (991 mg).

The sodium hyaluronate (700 mg) was then dissolved in a 0.1M sodium chloride solution (70 ml) and passed through a 70 ml column of an anion exchange resin (AGMP-1 (Cl⁻ type); BIO-RAD) which had preliminarily been equilibrated with a 0.1M sodium chloride solution. Elution with a variety of salt concentrations resulted in four fractions which contain a hyaluronic acid corresponding to the salt concentrations. These eluates respectively were added to 99.5% ethanol (1.5 liters). The precipitates thus obtained were dissolved in distilled water (10 ml) and passed through a membrane filter (0.22 ml). The eluate was added to 99.5% ethanol (100 ml). The precipitates thus obtained were washed with 95% ethanol, acetone and ether in sequence, and dried under reduced pressure to give the sodium hyaluronate (51) 255 mg, (52) 173 mg, 109 mg and 84 mg. These hyaluronates had a molecular weight of about 80,000, 170,000, 270,000 and 410,000, respectively, based on the gel filtration method with dextran as a standard material.

EXAMPLE 20

Sodium Hyaluronate-3'-N-(Gly-Gly-Phe-Gly)-DXR (53)

In the same manner as in Example 19, a solution of sodium hyaluronate (51) (150 mg) in a mixture of water:N,N-dimethylformamide (1:1) (12 ml), a solution of 3'-N-

Figure 17:
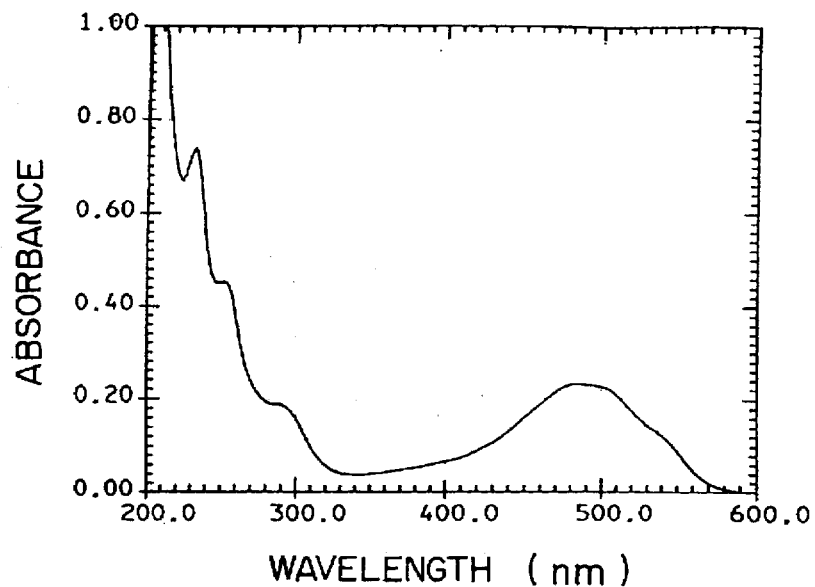
FIG. 17 illustrates an ultraviolet-visible absorption spectrum of sodium hyaluronate-3'-N-(Gly-Gly-Phe-Gly)-DXR (53) obtained in Example 20 (concentration: 181 µg/ml, solvent: water)
Figure 18:
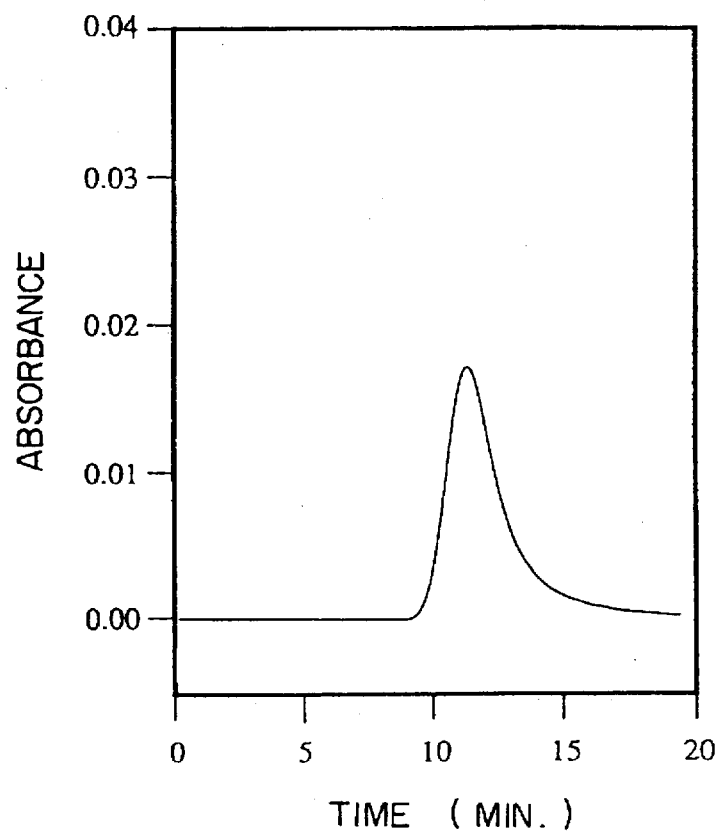
FIG. 18 illustrates an elution pattern by gel filtration of sodium hyaluronate-3'-N-(Gly-Gly-Phe-Gly)-DXR (53) obtained in Example 20 (detected by visible absorption at 478 nm)

(Gly-Gly-Phe-Gly)-DXR·HCl (10) (33 mg) in a mixture of water:N,N-dimethylformamide (1:1) (3 ml) and 1-ethoxycarbonyl-2-ethoxy-1,2-dihydroquinoline (150 mg) were reacted to give the title compound (53) (164 mg). The complex had a drug content of 6.2% determined by the visible absorption spectrophotometry at 478 nm and the total weight of the complex. The ultraviolet-visible absorption spectrum and the elution pattern of the gel filtration (detected by the visible absorption at 478 nm) are illustrated in FIGS. 17 and 18, respectively.

EXAMPLE 21

Sodium Hyaluronate-3'-N-(Gly-Gly-Phe-Gly)-DXR (54)

Reaction was carried out in the same manner as in Example 20, except that sodium hyaluronate (51) was replaced by sodium hyaluronate (52) to give the title compound (54) (163 mg). The complex had a drug content of 5.7% determined by the visible absorption spectrophotometry at 478 nm and the total weight of the complex.

EXAMPLE 22

Sodium Hyaluronate-3'-N-(Gly-Gly-Phe-Gly)-DXR (55)

In the same manner as in Example 19, a solution of sodium hyaluronate (100 mg) (derived from pig skin; Mw=40,000–60,000; manufactured by Seikagaku Co.) in a mixture of water:N,N-dimethylformamide (1:1) (12 ml), a solution of 3'-N-(Gly-Gly-Phe-Gly)-DXR·HCl (10) (22 mg) in a mixture of water:N,N-dimethylformamide (1:1) (2 ml) and 1-ethoxycarbonyl-2-ethoxy-1,2-dihydroquinoline (100 mg) were reacted to give the title compound (55) (87 mg). The complex had a drug content of 5.4% determined by the visible absorption spectrophotometry at 478 nm weight of the complex.

Some of referential examples are schematically illustrated as follows:

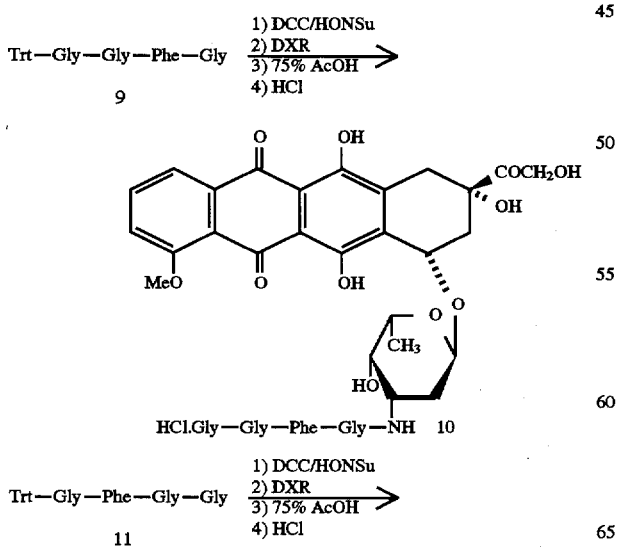

-continued

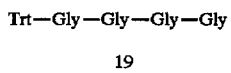

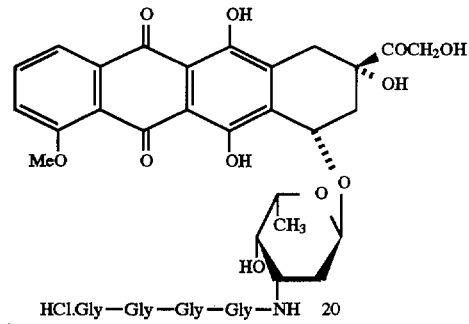

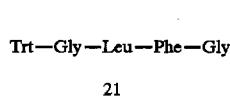

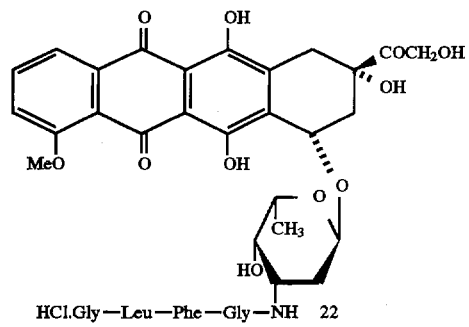

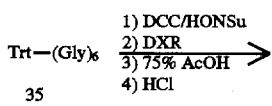

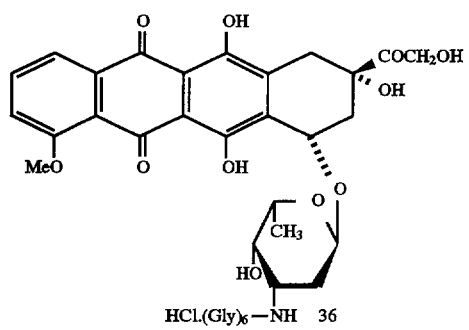

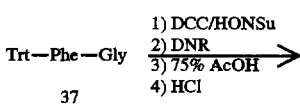

-continued

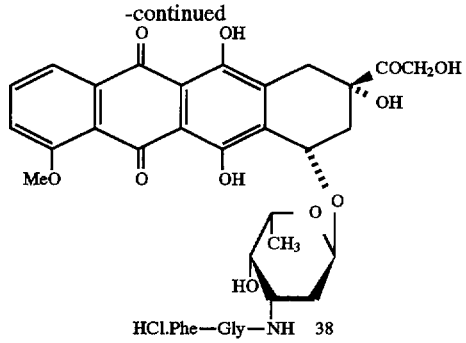

EXPERIMENTAL EXAMPLE 1

Anti-Tumor Activity

The Walker carcinosarcoma 256 cells ($1\times10^7$) were transplanted intramuscularly to the inguinal region of female Wistar rats (6 weeks old, 110±10 g). After three days, test compounds, the compound (27) obtained in Example 5, the compound (23) obtained in Example 1 or doxorubicin hydrochloride dissolved in physiological saline, were administered to the tail vein of five rats constructing a group. These compounds were administered in an amount of 51.2, 128, 320, and 800 µg/kg that were equivalented as doxorubicin.

After seven days from the transplantation of the tumor cells, rats were sacrificed by bloodletting. Tumor was excised and weighed to judge the anti-tumor activity.

Figure 19:
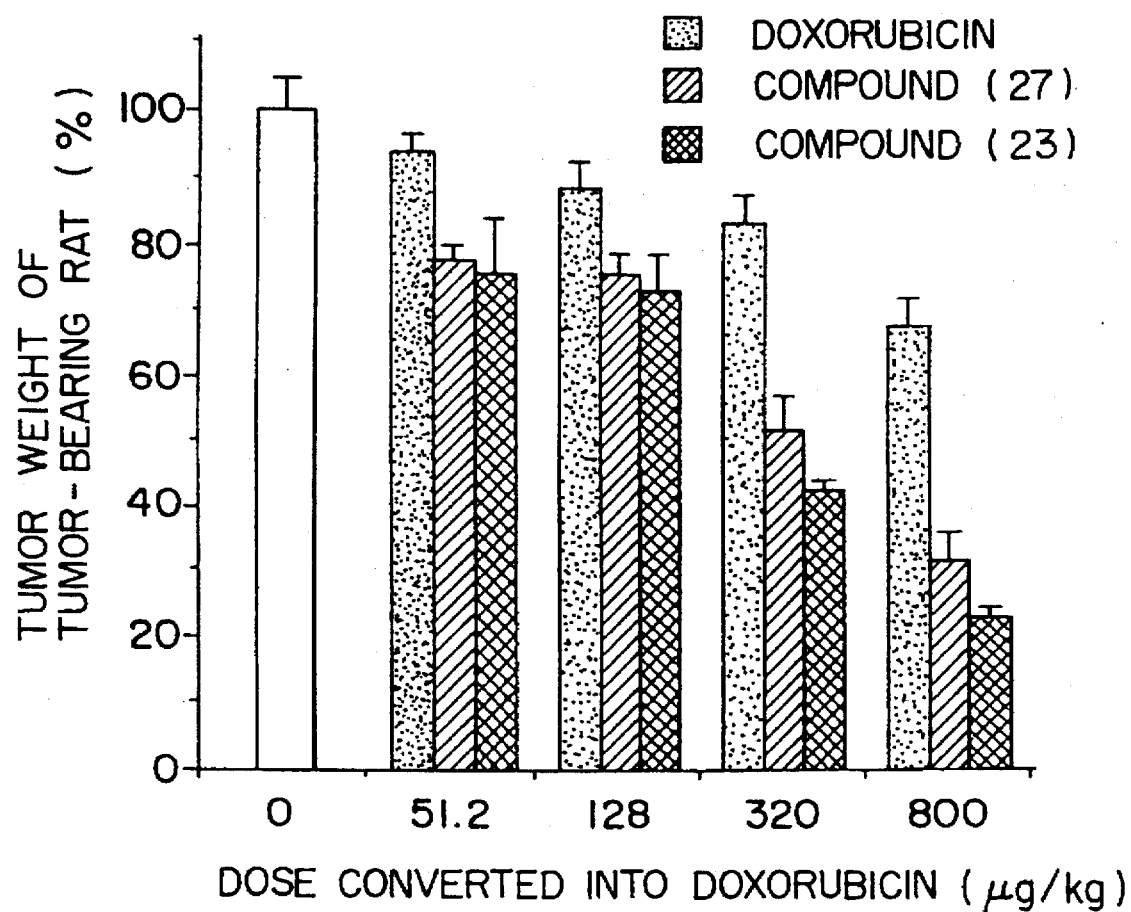
FIG. 19 is a graph which illustrates the relationship between the doses of the drug complex according to the present invention or doxorubicin and tumor weights.

The relationship between dose and tumor weight are illustrated in FIG. 19. As is apparent from FIG. 19, the drug complexes according to the present invention exhibited excellent anti-tumor activity as compared with doxorubicin in either doses.

EXPERIMENTAL EXAMPLE 2

Variation of Rat Weight

Test compounds, the compound (27) obtained in Example 5, the compound (23) obtained in Example 1 or doxorubicin dissolved in physiological saline, were administered to the tail vein of five Wistar female rats (6 weeks old, 110±10 g) constructing a group. Toxicity and side effect was evaluated by the change in body weight and survived life of the rats. The weight change of the rats was expressed as a percentage on the basis of the initial weights.

Figure 20:
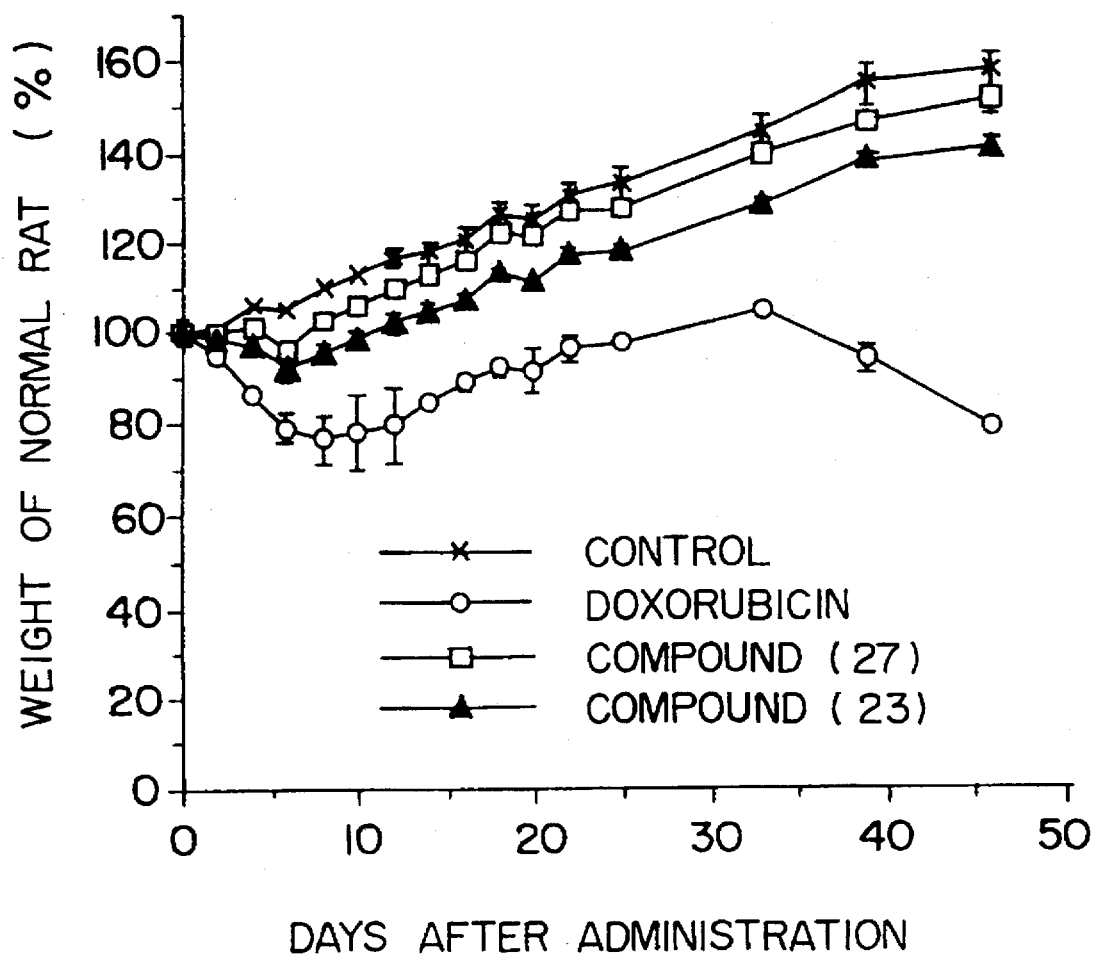
FIG. 20 is a graph which illustrates change in the body weight of normal rats to which the drug complex according to the present invention or doxorubicin has been administered.

The change of rat weight in the group that the compound was administered in an amount of 10 mg/kg is illustrated in FIG. 20. Body weight tended to decrease at the initial period after administration in both doxorubicin and the drug complexes according to the present invention. However, the changes in the drug complexes cases were slight as compared with that in doxorubicin. Furthermore, in the groups to which the drug complexes were administered, weight was increased again and recovered to a initial level at about 10 days after administration of the drug complex. On the other hand, weight was not recovered to a initial level, some rats were dead in the case of doxorubicin These results suggest that the complex according to the present invention shows increased anti-tumor activity and decreased toxicity and side effect compared with doxorubicin. Therefore, it was suggested that the drug complex according to the present invention may be a useful polymeric medication having an improved therapeutic index.

What is claimed is:

1. A polysaccharide derivative comprising a polysaccharide having a carboxyl group into which a peptide chain is introduced at a part or all of the carboxyl groups, the peptide chain comprising 1–8 amino acids where the amino acid may be the same or different, wherein a part or all of the amino groups in the peptide chain which are not involved in the linkages with the carboxyl groups of the polysaccharide or a part or all of the carboxyl groups in the peptide chain may form an acid amide linkage or an ester linkage with a carboxyl group, an amino group or a hydroxyl group of a third compound having the carboxyl group, the amino group or the hydroxyl group, or a salt thereof.

2. A polysaccharide derivative or a salt thereof according to claim 1, wherein the polysaccharide having a carboxyl group comprises a polysaccharide in which the hydrogen atom of a part or all of the hydroxyl group is substituted by a carboxy $C_{1-4}$ alkyl group, or in which a polybasic acid is introduced into a part or all of the hydroxyl groups through an ester linkage.

3. A polysaccharide derivative or a salt thereof according to claim 2, wherein the polysaccharide in which the hydrogen atom of a part or in which all of the hydroxyl group is substituted by a carboxy $C_{1-4}$ alkyl group or a polybasic acid is introduced into a part or all of the hydroxyl groups through an ester linkage is selected from the group consisting of pulullan, dextran, mannoglucan, mannan, chitin, inulin, levan, xylan and arabinan.

4. A polysaccharide derivative or a salt thereof according to claim 3, wherein the carboxy $C_{1-4}$ alkyl group is a carboxymethyl group.

5. A polysaccharide derivative or a salt thereof according to claim 3, wherein the polybasic acid is selected from the group consisting of succinic acid, maleic acid, glutaric acid, adipic acid, citraconic acid, cis-aconitic acid, L-aspartic acid, L-glutamic acid, malonic acid, fumaric acid and diglycolic acid.

6. A polysaccharide derivative or a salt thereof according to any one of claims 1–5, wherein said polysaccharide is pulullan, and the pulullan moiety has a molecular weight from $2 \times 10^3$ to $1 \times 10^6$, comprises the repeating unit represented by the formula (I):

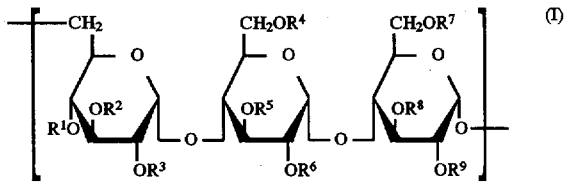

in which $R^{1-R9}$, which may be the same or different, respectively represent, a hydrogen atom, a group —$(CH_2)_m$—CO—X, a group —CO—$(CH_2)_n$—CO—X, or a group —CO—A—CO—X, where —CO—A—CO— represents a polybasic acid moiety of a polybasic acid from which the hydroxyl groups of two carboxyl groups have been removed, X represents a hydrogen atom or 8 peptide chain comprising 1–8 amino acids which may be the same or different, a part or all of the amino groups in the peptide chain which are not involved in the linkages with the carboxyl groups of the polysaccharide or the carboxyl groups in the peptide chain may form an acid amide linkage or an ester linkage with a carboxyl group, an amino group or a hydroxyl group of a third compound having the carboxyl group, the amino group or the hydroxyl group, m represents an integer of 1–4, and n represents an integer of 1–4.

7. A polysaccharide derivative or a salt thereof according to any one of claims 1–5, wherein said polysaccharide is chitin, and the chitin portion has a molecular weight from $2 \times 10^3$ to $1 \times 10^6$, comprises the repeating unit represented by the formula (II):

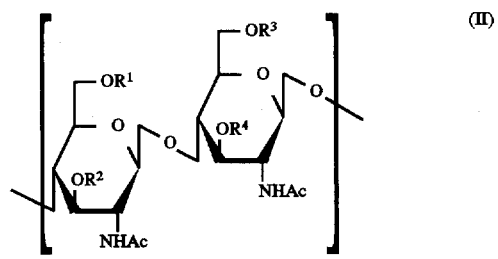

wherein $R^1$–$R^4$, which may be the same or different, respectively represent a hydrogen atom, a group —$(CH_2)_m$—CO—X, a group —CO—$(CH_2)_n$—CO—X, or a group —CO—A—CO—X, where —CO—A—CO— represents a polybasic acid moiety of a polybasic acid from which the hydroxyl groups of two carboxyl groups have been removed, X represents a hydrogen atom or a peptide chain comprising 1–8 amino acids which may be the same or different, a part or all of the amino groups in the peptide chain which are not involved in the linkages with the carboxyl groups of the polysaccharide or the carboxyl groups in the peptide chain may form an acid amide linkage or an ester linkage with a carboxyl group, an amino group or a hydroxyl group of a third compound having the carboxyl group, the amino group or the hydroxyl group, m represents an integer of 1–4, and n represents an integer of 1–4.

8. A polysaccharide derivative or a salt thereof according to any one of claims 1–5, wherein said polysaccharide is dextran, and the dextran portion has a molecular weight from $2 \times 10^3$ to $2 \times 10^6$, comprises the repeating unit represented by the formula (III):

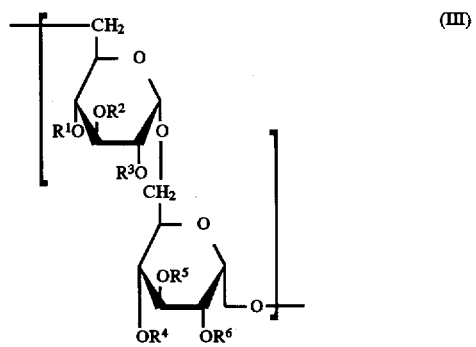

wherein $R^1$–$R^6$, which may be the same or different, respectively represent a hydrogen atom, a group —$(CH_2)_m$—CO—X, a group —CO—$(CH_2)_n$—CO—X, or a group —CO—A—CO—X, where —CO—A—CO— represents a polybasic acid moiety of a polybasic acid from which the hydroxyl groups of two carboxyl groups have been removed, X represents a hydrogen atom or a peptide chain comprising 1–8 amino acids which may be the same or different, a part or all of the amino groups in the peptide chain which are not involved in the linkages with the carboxyl groups of the polysaccharide or the carboxyl groups in the peptide chain may form an acid amide linkage or an ester linkage with a carboxyl group, an amino group or a hydroxyl group of a third compound having the carboxyl group, the amino group or the hydroxyl group, m represents an integer of 1–4, and n represents an integer of 1–4.

10. A polysaccharide derivative or a salt thereof according to claim 1, wherein the polysaccharide having a carboxyl group is selected from the group consisting of hyaluronic acid, pectic acid, alginic acid, chondroitin and N-acetyl-de-N-sulfated heparin, and a salt thereof.

11. A polysaccharide derivative or a salt thereof according to claim 1, wherein said polysaccharide is N-acetyl-de-N-sulfated heparin, and the heparin portion has a molecular weight from $2 \times 10^3$ to $6 \times 10^4$, comprises the repeating unit represented by the formula (V):

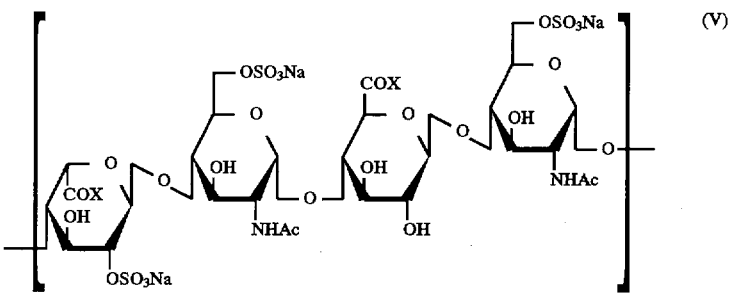

9. A polysaccharide derivative or a salt thereof according to any one of claims 1–5, wherein said polysaccharide is mannoglucan, and the mannoglucan portion has a molecular weight from $2 \times 10^3$ to $2 \times 10^6$, comprises the repeating unit represented by the formula (IV):

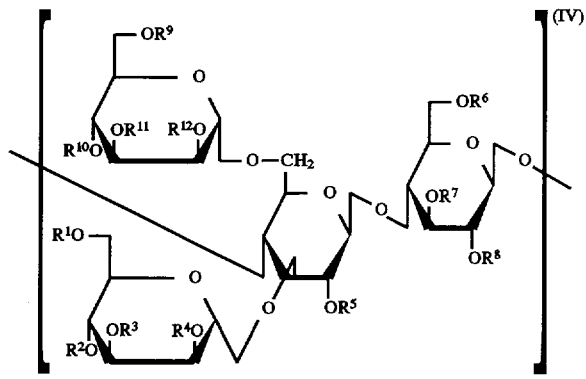

wherein $R^1$–$R^9$, which may be the same or different, respectively represent a hydrogen atom, a group —$(CH_2)_m$—CO—X, a group —CO—$(CH_2)_n$—CO—X, or a group —CO—A—CO—X, where —CO—A—CO— represents a polybasic acid moiety of a polybasic acid from which the hydroxyl groups of two carboxyl groups have been removed, X represents a hydrogen atom or a peptide chain comprising 1–8 amino acids which may be the same or different, a part or all of the amino groups in the peptide chain which are not involved in the linkages with the carboxyl groups of the polysaccharide or the carboxyl groups in the peptide chain may form an acid amide linkage or an ester linkage with a carboxyl group, an amino group or a hydroxyl group of a third compound having the carboxyl group, the amino group or the hydroxyl group, m represents an integer of 1–4, and n represents an integer of 1–4, and $R^{10}$–$R^{12}$, which may be the same or different, respectively represent the groups as defined in the groups $R^1$–$R^9$.

wherein X represents a peptide chain containing 1–8 amino acids, which may be the same or different, and a part or all of amino groups in the peptide chain which are not involved in the linkages with the N-acetyl-de-N-sulfated heparin or a part or all of carboxyl groups in the peptide chain may form an acid amide linkage or an ester linkage with a carboxyl group, an amino group or a hydroxyl group of a third compound having the carboxyl group, the amino group or the hydroxyl group.

12. A polysaccharide derivative or a salt thereof according to claim 1, wherein said peptide comprises 2–4 amino acids.

13. A polysaccharide derivative or a salt thereof according to claim 1, wherein the third compound having an amino group, a carboxyl group or a hydroxyl group is a drug.

14. A polysaccharide derivative or a salt thereof according to claim 13, wherein said drug is an anti-tumor agent.

15. A polysaccharide derivative or a salt thereof according to claim 14, wherein said anti-tumor agent is selected from the group consisting of doxorubicin and daunorubicin.

16. A polysaccharide derivative or a salt thereof according to claim 1, wherein said polysaccharide is hyaluronic acid, and the hyaluronic acid moiety has a molecular weight from $2 \times 10^3$ to $6 \times 10^4$, comprises the repeating unit represented by the formula (VI):

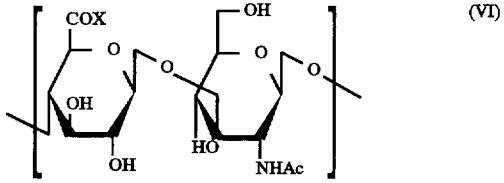

wherein X represents a peptide chain containing 1–8 amino acids, which may be the same or different, and a part or all of amino groups in the peptide chain which are not involved in the linkages with the N-acetyl-de-N-sulfated heparin or a part or all of the carboxyl groups in the peptide chain may form an acid amide linkage or an ester linkage with a carboxyl group, an amino group or a hydroxyl group of a third compound having the carboxyl group, the amino group or the hydroxyl group.

* * * * *